US010772740B2

(12) United States Patent
Poirters

(10) Patent No.: US 10,772,740 B2
(45) Date of Patent: Sep. 15, 2020

(54) CONTROL OF DIGITS FOR ARTIFICIAL HAND

(71) Applicant: HY5PRO AS, Raufoss (NO)

(72) Inventor: Josephus Martinus Maria Poirters, Faberg (NO)

(73) Assignee: HY5PRO AS, Raufoss (NO)

( * ) Notice: Subject to any disclaimer, the term of this patent is extended or adjusted under 35 U.S.C. 154(b) by 100 days.

(21) Appl. No.: 15/570,220

(22) PCT Filed: Apr. 29, 2016

(86) PCT No.: PCT/EP2016/059681
§ 371 (c)(1),
(2) Date: Oct. 27, 2017

(87) PCT Pub. No.: WO2016/174243
PCT Pub. Date: Nov. 3, 2016

(65) Prior Publication Data
US 2018/0140441 A1   May 24, 2018

(30) Foreign Application Priority Data
Apr. 30, 2015   (GB) .................................. 1507397.6

(51) Int. Cl.
*A61F 2/54*   (2006.01)
*A61F 2/58*   (2006.01)
(Continued)

(52) U.S. Cl.
CPC ................ *A61F 2/54* (2013.01); *A61F 2/586* (2013.01); *A61F 2/72* (2013.01); *B25J 9/104* (2013.01);
(Continued)

(58) Field of Classification Search
CPC .... A61F 2/50; A61F 2/58; A61F 2/586; A61F 2/68; A61F 2/54; B25J 13/082
See application file for complete search history.

(56) References Cited

U.S. PATENT DOCUMENTS 5,108,140 A   4/1992   Bartholet
5,378,130 A   1/1995   Ozeki et al.
(Continued)

FOREIGN PATENT DOCUMENTS

DE   10 2013 007539 A1   11/2014
EP       1195151 A1       4/2002
(Continued)

OTHER PUBLICATIONS

GB Search Report, GB Application No. GB1507394.3, dated Jun. 30, 2015, 3 pages.
(Continued)

*Primary Examiner* — Bruce E Snow
(74) *Attorney, Agent, or Firm* — McDonnell Boehnen Hulbert & Berghoff LLP

(57) ABSTRACT

A digit mechanism for an artificial hand comprises: a lower digit (44) arranged to be rotatably coupled to a palm unit (12) of the artificial hand; an upper digit (48) rotatably coupled to the lower digit (44); a lower digit rotation mechanism (34, 46, 52, 58) for applying a moment to the lower digit (44) to rotate the lower digit (44) relative to the palm unit (12); an upper digit rotation mechanism (50, 54, 56) for applying a moment to the upper digit (48) to rotate the upper digit (48) relative to the lower digit (44); and a force balancing mechanism (60, 58) for mechanically adjusting the magnitude of the moment applied by the lower digit rotation mechanism (34, 46, 52, 58) and/or the upper digit rotation mechanism (50, 54, 56) in accordance with the magnitude(s) of outside forces resisting rotation of the upper digit (48) and/or the lower digit (44) in order to preferen-
(Continued)

tially apply movement to the digit experiencing lower resistance to movement; wherein the force balancing mechanism is arranged to increase the force applied to rotate a controlled digit when a controlling digit experiences a greater resistance to movement than the controlled digit, and decrease the force applied to rotate the controlled digit when the controlling digit experiences a lesser resistance to movement than the controlled digit; wherein the lower digit rotation mechanism (34, 46, 52, 58) and upper digit rotation mechanism (50, 54, 56) are arranged to be mechanically actuated, in use, by a force applied from a single actuator at the palm unit (12).

21 Claims, 10 Drawing Sheets

(51) Int. Cl.
| | | |
|---|---|---|
| *B25J 9/10* | | (2006.01) |
| *B25J 15/00* | | (2006.01) |
| *A61F 2/72* | | (2006.01) |
| *A61F 2/68* | | (2006.01) |
| *A61F 2/74* | | (2006.01) |
| *B25J 13/08* | | (2006.01) |
| *B25J 15/08* | | (2006.01) |

(52) U.S. Cl.
CPC ... *B25J 15/0009* (2013.01); *A61F 2002/6818* (2013.01); *A61F 2002/6845* (2013.01); *A61F 2002/74* (2013.01); *A61F 2002/742* (2013.01); *A61F 2002/745* (2013.01); *A61F 2002/748* (2013.01); *B25J 13/082* (2013.01); *B25J 15/08* (2013.01)

(56) References Cited

U.S. PATENT DOCUMENTS

| | | | |
|---|---|---|---|
| 8,951,303 B2 | 2/2015 | Dehoff et al. | |
| 8,991,884 B2 * | 3/2015 | DeLouis | B25J 15/0009 294/106 |
| 2007/0198098 A1 | 8/2007 | Roston et al. | |
| 2008/0247844 A1 | 10/2008 | Hartrampf et al. | |
| 2012/0203358 A1 | 8/2012 | Lind et al. | |
| 2013/0033053 A1 | 2/2013 | Wilkinson et al. | |
| 2013/0331949 A1 | 12/2013 | Dehoff et al. | |
| 2014/0003987 A1 | 1/2014 | Martin-Dye | |
| 2014/0288664 A1 | 9/2014 | Miyazawa | |

FOREIGN PATENT DOCUMENTS

| | | |
|---|---|---|
| EP | 2612619 A1 | 10/2013 |
| GB | 678470 | 9/1952 |
| GB | 2102888 | 2/1983 |
| JP | 2003305681 A | 10/2003 |
| WO | 2011/022569 A1 | 2/2011 |
| WO | 2011/072750 A1 | 6/2011 |
| WO | 2012/129288 A2 | 9/2012 |

OTHER PUBLICATIONS

PCT International Search Report and Written Opinion, PCT International Application No. PCT/EP2016/059679, dated Jul. 7, 2016, 9 pages.
Belter, Joseph T. et al., "Mechanical Design and Performance Specifications of Anthropomorphic Prosthetic Hands: A Review", JRRD, vol. 50,. No. 5, 2013, pp. 599-618.
GB International Search Report, GB Application No. GB1507397.6, dated Jul. 1, 2015, 3 pages.
PCT International Search Report and Written Opinion, PCT International Application No. PCT/EP2016/059681, dated Aug. 26, 2016, 14 pages.
GB International Search Report, GB Application No. GB1507399.2, dated Jul. 16, 2015, 4 pages.
PCT International Search Report and Written Opinion, PCT International Application No. PCT/EP2016/059678, dated Jul. 7, 2016, 9 pages.
Official Action dated Feb. 12, 2020, issued in corresponding Japanese Patent Application No. 2017-557106, 22 pages.

* cited by examiner

CONTROL OF DIGITS FOR ARTIFICIAL HAND

CROSS REFERENCE TO RELATED APPLICATIONS

The present application is a national stage entry of PCT/EP2016/059681, filed 29 Apr. 2016, and claims priority to GB 1507397.6 filed 30 Apr. 2015. The full disclosures of PCT/EP2016/059681 and GB 1507397.6 are incorporated herein by reference.

The present invention relates to a digit mechanism for an artificial hand, for example a prosthetic hand used to replace a person's missing hand, and to a related method. In some example embodiments the digit mechanism is combined with similar devices and with further features including a palm unit in order to form an artificial hand.

There is an on-going demand for improvements in artificial hands not only for use as prosthetics but also in relation to robotics and automated handling devices that can mimic the dexterity of the human hand. The last few decades have seen great advances in relation to myoelectric artificial hands, which use electromyography signals or potentials from voluntarily contracted muscles within a person's residual limb to control the movements of the hand. A sensor or multiple sensors are placed on the surface of the skin to receive the signals. Some time ago Otto Bock (Otto Bock HealthCare Deutschland GmbH of Duderstadt, Germany, www.ottobock-group.com) designed a wrist connector unit that has become a standard in the field of myoelectric artificial hands. Devices also exist that use electromechanical switches actuated by body movements in order to control the artificial hand.

A review of the current state-of-the-art in relation to anthropomorphic prosthetic hands can be found in "Mechanical design and performance specifications of anthropomorphic prosthetic hands: A review" by Joseph T. Belter et al, JRRD, volume 50, number 5, 2013, pages 599-618. As discussed in that review, a number of companies are active in the field and have commercial products on the market. The commercial products make use of various combinations of electrical motors and mechanical couplings to actuate the fingers and thumb of the hand with varying degrees of freedom. Whilst these commercially available hands can in some cases provide a suitable level of dexterity for an artificial hand for use as a prosthetic hand they generally suffer from excessive weight, causing discomfort for the user, and they are complex and expensive.

Hydraulically actuated hands have also been proposed, although to date no commercial product is known to exist. A hand design known as "Fluidhand" has been developed at the Karlsruhe Institute of Technology (KIT) as a prototype that has been tested in the Orthopaedic University Hospital in Heidelberg. This hand uses miniature hydraulics within the fingers in an attempt to provide a large degree of freedom of movement (and hence dexterity) in an alternative manner to the commercial electromechanical hands. However, the "Fluidhand" is operated at a rather low pressure (9 to 10 bar) and this means that the gripping force is relatively low. Another disadvantage is the use of externally mounted hoses and couplings, which are vulnerable to damage and mean that the hand is not sufficiently robust for everyday use as a prosthetic. There is also a significant risk of leakage of the hydraulic fluid.

Further proposals for the use of hydraulics are found in patent publications. US 2012/203358 discloses a mesofluidic powered finger using high-pressure low-volume hydraulics to actuate each individual joint of a finger. This proposal is considered to suffer from similar disadvantages to the "Fluidhand".

U.S. Pat. No. 8,951,303 proposes the use of hydraulics along with a mechanical finger joint. The fingers are actuated by tendon cables in a way similar to some of the commercially available electromechanical prosthetic hands, and a pair of mesofluidic hydraulic pistons control movement of each finger joint. Although this system addresses some of the issues with fully hydraulic artificial hands, there are still problems that remain. The strength of the group that can be produced is constrained due to the nature of the hydraulic system, and the requirement for multiple hydraulic pistons for each finger results in a significant degree of complexity leading to costly production and a risk of leakage.

Another example of a combination of hydraulic and mechanical elements is found in WO 2011/072750, which describes a hand having mechanical tendon cable actuated finger joints moved via a single hydraulic piston for each finger. In order to allow for both a fast finger movement and high grip strength WO 2011/072750 proposes the use of two hydraulic pumps providing the possibility of high pressure and low pressure operation of the hydraulic elements. The lower pressure hydraulic pump is decoupled from the motor/hydraulics via a clutch and isolating valve in order to allow the high pressure hydraulic pump to control the finger movement. The system is arranged to do this automatically when the gripping pressure increases above the threshold. This hand will hence begin with a fast movement to bring the fingers into contact with an object at a lower gripping pressure, and then switch to a slower higher pressure movement to increase the strength of the grip. In addition, the various pistons that actuate the fingers are all coupled together and this means that the different fingers will close to a different degree depending on the resistance that they meet from a gripped object as the pressure is maintained equally across each hydraulic piston, and the greatest gripping force on the object is not applied until all of the fingers have closed about the object.

The hand disclosed in WO 2011/072750 is considered to represent a significant advance compared to other known hydraulically powered artificial hands, but it still suffers from potential problems. The hand is relatively bulky and complex and yet still does not provide significant advances in the control of finger movement for the user. Hence there remains a need for improvements in relation to artificial hands of this type.

Viewed from a first aspect, the present invention provides a digit mechanism for an artificial hand, the digit mechanism comprising: a lower digit arranged to be rotatably coupled to a palm unit of the artificial hand; an upper digit rotatably coupled to the lower digit; a lower digit rotation mechanism for applying a moment to the lower digit to rotate the lower digit relative to the palm unit; an upper digit rotation mechanism for applying a moment to the upper digit to rotate the upper digit relative to the lower digit; and a force balancing mechanism for mechanically adjusting the magnitude of the moment applied by the lower digit rotation mechanism and/or the upper digit rotation mechanism in accordance with the magnitude(s) of outside forces resisting rotation of the upper digit and/or the lower digit in order to preferentially apply movement to the digit experiencing lower resistance to movement; wherein the force balancing mechanism is arranged to increase the force applied to rotate a controlled digit when a controlling digit experiences a greater resistance to movement than the controlled digit, and decrease the force applied to rotate the controlled digit when the controlling digit experiences a lesser resistance to movement than the controlled digit; and wherein the lower digit rotation mechanism and upper digit rotation mechanism are arranged to be mechanically actuated, in use, by a force applied from a single actuator at the palm unit.

With this arrangement the digits can be controlled for an adaptive grip with only a single actuator at the palm unit applying a single force to the digit mechanism. When one of the digits, acting as the controlling digit, meets with increasing resistance then the force balancing mechanism adjusts the distribution of forces so that the other digit, i.e. the controlled digit, receives a greater proportion of the force supplied to the digit mechanism, and is therefore rotated relatively more. In this way it becomes possible to ensure that both digits move to come in contact with an object, even when the object is of an irregular shape, for example to close the digits around an object when an artificial hand using the digits is gripping the object. The mechanism may be set with a default pattern of movement when there is no resistance to rotation of the digits, for example in order to close the hand using the digit mechanism into a pincer grip, and when the first digit comes into contact with an object to be gripped or with another source of resistance to movement then the proportion of force supplied to that digit is reduced compared to the amount of force supplied to the remaining digit, thereby ensuring that both digits will close against the resistance to movement with generally equal pressure. This ensures that a firm grip can be achieved in a similar way to a natural hand, with the digit mechanism making use of all of the digits to form the grip. It also means that the user can very easily "shape" an artificial hand into a required grip pattern or pose by selectively resisting the motion of different digits using the above digit mechanism.

Unlike known digit mechanisms with adaptive capabilities there is no need for multiple actuators and complicated microprocessor control. Instead, a single actuator can be used. In addition, in contrast to known digit mechanisms using a single actuator input and tendon type connections, the relative degree of movement of the upper and lower digits can vary and is not fixed by gearing or the like. The proposed digit mechanism also allows for a much more robust construction, and in particular the ability to introduce a spring back type arrangement. Thus, the digit mechanism may be arranged to flex in response to outside forces and to be able to be pushed and moved in the closing direction resiliently, thereby minimising the risk of damage to the digit mechanism and other elements of an artificial hand in which it may be incorporated.

As used herein, the term upper digit references a digit of the artificial finger or thumb closer to its distal end, i.e. closer to the tip of the finger or thumb, and the term lower digit references a digit of the finger or thumb at the proximal end, i.e. closest to the palm. The terms upper and lower are used in a similar way below to refer to other parts of the mechanism. The digit mechanism may form the basis for a finger or a thumb of the artificial hand.

There may be just two moveable digits in the digit mechanism and in that case the upper digit is the distal digit and would move with the tip of the finger or thumb. It would be possible to expand to have three digits by adding a further rotation mechanism and a further force balancing mechanism described below so that a further digit was included between the lower digit and the uppermost digit. Thus there may be a lower digit, a first upper digit rotatably coupled to the lower digit at a lower end of the first upper digit, and a second upper digit rotatably coupled to an upper end of the first upper digit, with an additional rotation device for applying a moment to the additional upper digit and an additional a lower pulley as described above, a first upper pulley interacting with the lower pulley and a first clutch mechanism provided at the lower pulley as described above, and also a second clutch mechanism at the first upper pulley interacting with a second upper pulley and other repeated elements to create a further system for adaptive movement of the second upper digit. This allows for movement of three digits as with a natural finger and thereby may allow for an even more natural adaptive finger movement.

In order to generate the required adaptive grip the force balancing mechanism mechanically adjusts the magnitude of the moment applied by the lower digit rotation mechanism and/or the upper digit rotation mechanism in accordance with the magnitude(s) of outside forces resisting rotation of the upper digit and/or the lower digit and as a result the two rotation mechanisms preferentially apply movement to the digit experiencing lower resistance to movement. This is achieved by increasing the force applied to rotate a controlled digit when a controlling digit experiences a greater resistance to movement than the controlled digit, and decreasing the force applied to rotate the controlled digit when the controlling digit experiences a lesser resistance to movement than the controlled digit. The controlling digit may be the upper digit and the controlled digit the lower digit, or vice versa. The first option is used in an example embodiment described herein. With the typical geometry required for an artificial hand that follows the aesthetics of the human hand then there is more space available for installation of mechanisms at the proximal end, and since in general a more complex mechanism is required to adjust the amount of force applied to rotate a digit than to react to the amount of force that resists rotation of digit then an arrangement using the lower digit as the controlled digit can more easily be designed without adverse impact on the aesthetics of the artificial hand. There is hence a slight advantage to arranging the mechanism in that way.

The force balancing mechanism may include a clutch for transmission of a varying amount of power for rotation of the controlled digit with the clutch being controlled to adjust the varying amount of power in accordance with the degree of resistance to motion of the controlling digit. The use of a clutch in this way allows for an effective control of the proportion of power used to move one digit as compared to the other. To control the clutch the force balancing mechanism may include a clutch controller, preferably a mechanical device that is moved in accordance with the magnitude of the resistance to movement of the controlling digit. In the digit mechanism since the upper digit rotation mechanism and the lower digit rotation mechanism are mechanically actuated then an increase in resistance to movement of a digit will increase the forces in the respective rotation mechanism, for example increasing a torque, tension, compression, and/or strain in elements of the mechanism. It is preferred for the clutch controller to be moved by a force of this type. In one example the digit rotation mechanism for the controlling digit is actuated by a cable, such that increased resistance to rotation of the digit will increase the tension in the cable. In this case the clutch controller may include a mechanical device that is moved in accordance with the tension in the cable, such as a lever that the cable passes over in a V-shape. With this arrangement tension in the cable will tend to pull the lever, allowing the lever to be moved in accordance with the magnitude of the resistance to movement of the controlling digit. Other mechanisms would of course be possible.

The force balancing mechanism may include an adjustment/calibration mechanism for adjusting the balance in forces, for example to ensure a pincer type grip when there is no resistance to motion as described above. The clutch may be any mechanism able to control the amount of power used for rotation of the controlled digit in comparison to the amount of power used for rotation of the controlling digit. It is preferred for the clutch to include the adjustment/calibration mechanism. A person skilled in the art will appreciate that there are numerous ways that such clutch could be implemented. In a preferred embodiment a band brake is used. This has been found to provide a lightweight and easily miniaturisable clutch, and these are important advantages for an artificial hand where, as discussed above, the size and weight are significant. A band brake as the clutch may be combined with a lever and cable arrangement of the type discussed above as the clutch controller, with the lever acting to tighten the band brake in accordance with increasing tension in the cable. This has again been found to be a mechanism that provides a small and lightweight solution, as well as being robust and easily implemented within the geometry of artificial digits. The band brake may include an adjustment/calibration mechanism as described above, for example through a screw adjuster that adjusts the tightness of the band brake independently of the adjustment applied by the clutch controller (for example the lever discussed above).

The digit rotation mechanisms for the upper and lower digit may include pulley and cable systems. One possibility includes a main cable for receiving a tension force from an actuator in the palm unit and for transferring this to a lower pulley about which the lower digit is arranged to rotate; and a secondary cable also coupled to the lower pulley and arranged to transfer a rotating movement of the lower pulley to an upper pulley about which the upper digit is arranged to rotate. The main cable and the secondary cable could be formed as a single cable wrapped around the lower pulley or otherwise attached thereto. However, it is advantageous to use separate cables so that they may separately be disconnected from the lower pulley, as this makes it easier to assemble the device and simpler to remove different individual parts, for example for maintenance. The use of cables and pulleys in this way has an advantage in that the digit can freely be pushed toward the closed position, i.e. creating slack in the cables, without risk of damage to the mechanism. This means that when they are mounted on a palm unit to form an artificial hand the digits are resistant to damage from impacts.

With the use of pulleys as above the force balancing mechanism may be arranged either to adjust the amount of force transferred between the upper pulley and upper digit in accordance with resistance to motion of the lower digit around the lower pulley, or to adjust the amount of force transferred between the lower pulley and the lower digit in accordance with resistance to motion of the upper digit around the upper pulley. As noted above there are considered to be advantages in having the force balancing mechanism constructed at the lower end of the digit mechanism, and therefore further details will be discussed in the context of a system focused on the lower pulley. It should be appreciated that the opposite arrangement could also be used.

When the force balancing mechanism is arranged to adjust the forces transferred from the lower pulley to rotate the lower digit then the tension in the main cable and the secondary cable may be linked by their connection to the lower pulley, and the upper pulley may be coupled to and rotate with the upper digit, i.e. so that the upper digit has the same degree of rotation as the upper pulley and is actuated by rotation of the upper pulley, with the lower pulley coupled to the lower digit with a clutch of the force balancing mechanism for partial transfer of the rotation force from the lower pulley to the lower digit. The clutch may be as described above. Thus, in one example there may be a lever as a clutch controller, with the secondary cable passing over the lever in a V shape between the lower pulley and upper pulley, such that increased resistance to movement of the upper digit will increase the tension in the secondary cable and pull the lever to increase the force transferred between the lower pulley and the lower digit by the clutch. The force balancing mechanism may include a band brake as the clutch in this case, with the band brake being arranged to control the amount of force transferred between the lower pulley and the lower digit; and the lever acting to tighten the band brake. Advantageously, the band brake and lower pulley can be accommodated in a relatively large "knuckle" at the lower end of the lower digit, with the lever and the V-shaped cable being placed within the lower digit extending toward the upper pulley, which is accommodated in a relatively small "knuckle" where the lower digit and upper digit join each other. The digit mechanism can include these features without needing to be oversized compared to a normal artificial hand, i.e. whilst being able to generally match the size of the digits of the patient's natural hand.

The digits may include housing elements formed as hollow digit-like shapes. A preferred example uses 3-D printed metal alloy, for example 3-D printed titanium, in order to form the digits. This provides the required structural strength whilst also allowing for complex shapes which minimise the need for additional machining when manufacturing the digit mechanism and fitting the various mechanical parts together.

The invention further extends to an artificial hand wherein multiple digit mechanisms as described above are mounted to a palm unit. The artificial hand may be a prosthetic hand and hence may include a cosmetic glove. The palm unit may include actuators for the digit mechanisms, for example actuators arranged to apply tension to main cables of the digit mechanisms or to otherwise apply rotation to the digits. The palm unit may potentially use electromechanical actuators, but this is considered to use too much weight and also it makes it harder to them implement a fully adaptive grip for the hand. Consequently, it is preferred for the digit mechanisms to be actuated by hydraulic actuators within the palm unit. This combination of mechanical fingers and thumb with a hydraulic palm unit is considered to provide the optimum design for minimal size and weight. There are currently no commercially available hands that use a combination of hydraulic and mechanical elements in this way.

Preferably the digit mechanism includes an attachment point for a spring that, in use, urges the digit towards the open position. When the digit mechanism is combined with an artificial hand then a spring may be mounted between the attachment point and a corresponding attachment point on the palm unit of the artificial hand. The spring allows for the digits to be resiliently pushed toward the closed position, returning to the open position when any forces are released. The digits can hence be arranged to freely close in relation to an impact or other outside force, and to then return to the open position (or to a position set by the relevant actuator) when the outside force is removed.

The lower digit may include a pivot arrangement for mounting to a bracket on a palm unit of the artificial hand, and preferably the pivot arrangement is formed along the same axis of rotation as elements of the lower digit rotation mechanism, for example the lower pulley and clutch as described above. When the digit mechanism is combined with an artificial hand then it may be mounted to the palm unit via coupling of the pivot arrangement to a bracket on the palm unit. Advantageously, multiple digit mechanisms for the fingers may be mounted to brackets that are aligned along the same axis of rotation, thereby allowing a single pin or shaft to secure all of the fingers to the palm unit.

It is preferred for the palm unit to use hydraulic actuators and for the actuators to be coupled together for distribution of pressure between them, thereby allowing an adaptive grip that will react to differences in resistance to motion of the different digit mechanisms, as well as reacting to differences in resistance to motion of different digits of each digit mechanism.

A possible arrangement for a palm unit includes: a palm unit body; a motor held by the palm unit body; a hydraulic pump assembly held by the palm unit body and comprising a low-pressure hydraulic pump and a high-pressure hydraulic pump, wherein both hydraulic pumps are powered simultaneously by the motor; and a hydraulic circuit held by the palm unit body and coupled to both hydraulic pumps.

The hydraulic circuit preferably has a low-pressure configuration in which the discharge sides of both hydraulic pumps are coupled to one or more hydraulic actuator(s) for the artificial hand and a high-pressure configuration in which the discharge side of the low-pressure pump is isolated from the hydraulic actuator(s) and recirculates fluid to the suction side of the low pressure pump with the discharge side of the high-pressure pump remaining coupled to the hydraulic actuator(s). The hydraulic circuit may advantageously be arranged to switch from the low-pressure configuration to the high-pressure configuration automatically during a closing grip pattern when the pressure in the system increases beyond a threshold value.

The above arrangement provides a palm unit capable of effective control of the artificial hand both with a fast low-pressure movement and a slow high-pressure movement, with the switching between low strength and high strength being automatic in reaction to pressure building up in the system, which advantageously can allow the system to automatically react to resistance when the artificial hand is gripping an object.

In order to switch from the low-pressure configuration to the high-pressure configuration automatically when the pressure in the system increases beyond a threshold value the hydraulic circuit may include a pressure controlled mechanism, for example a pressure controlled valve arranged to open when the pressure increases beyond the threshold value whilst the user is closing the hand. The threshold value might be a value between 10 and 15 bar, for example.

In one example hydraulic circuit the discharge side of the low-pressure pump is coupled to the discharge side of the high-pressure pump via a one-way valve permitting flow from the low-pressure pump toward the high-pressure pump and the discharge side of the low-pressure pump is coupled to the suction side of the low-pressure pump via the pressure controlled valve. With this arrangement, when the pressure at the discharge side of the low-pressure pump increases above the threshold value then the pressure controlled valve will open allowing for fluid to recirculate from the discharge side of the low-pressure pump to the suction side of the low-pressure pump, and resulting in closure of the one-way valve due to the higher pressure at the discharge side of the high-pressure pump. This means that discharge side of the high-pressure pump will remain coupled to the hydraulic actuators as required, whereas the low-pressure pump will be switched to operating in a recirculating mode.

It is preferred for the one-way valve to be able to be held open, for example to allow for reverse flow of fluid through the circuit during opening of the hand. The one-way valve may be an electromagnet controlled valve. The palm unit may include a controller such as a microprocessor for controlling the electromagnet controlled valve. This can be utilised to hold the valve open, for example when opening the hand requires reverse movement of hydraulic fluid through the circuit.

The motor may be a variable speed motor. This allows the user to control the volume of fluid pumped by the hydraulic pumps with only a single sensor input, and hence the user can have complete control of the speed of operation of the hand without the need for multiple sensors and/or complicated microprocessor routines.

A reversible motor may be used, thereby permitting close control by the user of opening and closing of the hand by forward and reverse operation of the hydraulic pumps. Preferably the motor is both variable speed and reversible.

Typically there would be multiple hydraulic actuators, for example to allow for control of multiple digit mechanisms for one or more fingers and the thumb. Preferably the hydraulic circuit is arranged so that the pressure and suction side of each of the hydraulic actuators is linked to equalise the pressure in the hydraulic fluid within multiple actuators, preferably within all actuators. This allows for adaptive movement of the digit mechanisms for the individual fingers and the thumb, whereby the finger or thumb will stop when it meets resistance with the other fingers or the thumb continuing to move until the grip is completed.

In preferred embodiments there are fewer hydraulic actuators than the number of fingers and thumbs on the hand, for example with only some of the fingers having a digit mechanism and one or more fingers have a passive mechanism without a dedicated hydraulic actuator. Naturally, the artificial hand would typically be arranged to have four fingers and one thumb. Preferably the palm unit does not include a separate hydraulic actuator for the little finger and optionally also it does not include a separate hydraulic actuator for the ring finger. In some examples the fingers without their own hydraulic actuator are resiliently coupled to an adjacent finger which does have an actuator. For example, the little finger and ring finger may be resiliently coupled to the middle finger, with the middle finger having a dedicated hydraulic actuator. In a preferred arrangement the palm unit includes three hydraulic actuators, being for the thumb, the index finger and the middle finger. This arrangement is in contrast to WO 2011/072750 which has hydraulic actuator for each of the fingers. It has been found that there is no significant disadvantage in terms of grip pattern when the little finger and optionally the ring finger are not provided with their own dedicated hydraulic actuator, and that any disadvantages outweighed by the advantage in reductions in size, weight and complexity of the artificial hand. The hydraulic actuators may be hydraulic cylinders.

In a preferred embodiment the hand includes a hydraulic cylinder for the thumb and multiple hydraulic cylinders for the fingers, and the bore size of the hydraulic cylinder for the thumb is larger than the bore size for the hydraulic cylinders of the fingers. Preferably the bore sizes are set so that the force that can be applied by the thumb is balanced with the forces from each of the fingers combined. This means that when the hand is closed then the force from the thumb side of the grip will balance with the force from the finger side of the grip.

The high-pressure pump may be arranged to operate at relatively low volumes and the low-pressure pump may be arranged to operate at relatively high volumes. This enables a quick low strength movement and a slow high-strength movement, which mimics natural use of the hand when gripping an object.

The hydraulic pump assembly may be formed as a single unit including both hydraulic pumps and being arranged to fit within a single chamber in the palm unit. The hydraulic pump assembly may be arranged with a prismatic shape for fitting into a chamber in the palm unit with a corresponding prismatic shape. A preferred arrangement uses a cylindrical shape for ease of manufacture and ease of assembly, as well as in order to ensure that a good seal can be obtained.

Preferably the pump assembly is sealed from the outside world within the palm unit. The pump assembly may include a seal, or a groove for holding a seal, at one end of the hydraulic pump assembly. This allows the entire hydraulic pump assembly to be accurately sealed within the chamber in the palm unit. The seal may for example be an O-ring type seal. By fully sealing the pump assembly within the palm unit it becomes possible to dispense with some of the seals that would otherwise be required between the two parts of the pump assembly since any leakage would be internal and therefore does not create a problem. The disadvantage of potential internal leakage is outweighed by the advantage in the reduction in size and weight of the pump, which as noted above is highly important for an artificial hand. In one example the pump assembly includes a hydraulic axle seal for the shaft between the two pumps, but does not include any seals between pump plates of the pumps. Preferably both of the hydraulic pumps are actuated by a single drive shaft assembly powered by the motor. The drive shaft assembly may include a shaft passing along an axis of the pump assembly. Thus, a shaft powered by the motor may pass through one of the pumps in order to reach the other pump. This shaft may be split in two, having a low-pressure section and high-pressure section driving the respective hydraulic pump, with axial play between the two sections. This has the advantage that the mechanical elements of the pump are axially isolated from one another.

In a preferred embodiment the pump assembly is assembled from a number of pump plates assembled together and held with bolts extending through the length of the pump assembly. Preferably the shaft also passes through the length of the pump assembly. The pump assembly may be generally cylindrical in form and it may be arranged to be inserted within a cylindrical chamber in the palm unit. The sealing between the pump and the outside world may be provide by an O-ring type seal or similar.

The palm unit body may form a sealed enclosure for the hydraulic circuit and hydraulic pump assembly, thereby containing all hydraulic parts. Preferably the motor is also contained within the palm unit body. The palm unit body is preferably formed in a single piece and in a preferred example it is formed by 3-D printing. It is preferred for all hydraulic connections for the hydraulic circuit to be formed by channels within a single piece palm unit body. This arrangement is particularly effective when combined with 3-D printing since the use of 3-D printing allows a very complicated shape to be formed with numerous internal features. By retaining all hydraulic connections between the various parts within the palm unit body it becomes straightforward to fully seal all hydraulic elements and ensure that the hydraulic system is robust and not at risk of damage or leakage.

The hydraulic circuit may include a locking valve in order to hold pressure within the hydraulic actuators when the motor has stopped. Advantageously this can allow for the palm unit to maintain the fingers and thumb in a locked grip position without the need to run the motor continually.

Preferably the palm unit is arranged to operate based on inputs from myoelectric sensors such as EMG sensors. In a preferred embodiment the level of tension in the user's muscle is used to control motor speed, which means that a single sensor can provide a great degree of control of the grip from the hand. This can avoid the need for a complicated programmable microprocessor. In one preferred example the palm unit is arranged to operate based on inputs from two EMG sensors, one of which is actuated to open the hand and the other of which is actuated to close the hand.

The palm unit may include a wrist connector. In particular it is preferred to use a quick connect type wrist connector. An Otto Bock type quick connect may be used. Using this type of standard connector allows the hand to be easily tried out by existing users of prosthetic hands.

Viewed from a second aspect, the invention provides a method for control of a digit mechanism of an artificial hand wherein the digit mechanism comprises: a lower digit arranged to be rotatably coupled to a palm unit of the artificial hand; an upper digit rotatably coupled to the lower digit; a lower digit rotation mechanism for applying a moment to the lower digit for rotating the lower digit relative to the palm unit; an upper digit rotation mechanism for applying a moment to the upper digit for rotating the upper digit relative to the lower digit; the method comprising: mechanically actuating the lower digit rotation mechanism and upper digit rotation mechanism using a force applied from a single actuator at the palm unit; and mechanically adjusting the magnitude of the moment applied by the lower digit rotation mechanism and/or the upper digit rotation mechanism in accordance with the magnitude(s) of outside forces resisting rotation of the upper digit and/or the lower digit in order to preferentially apply movement to the digit experiencing lower resistance to movement, thereby increasing the force applied to rotate a controlled digit when a controlling digit experiences a greater resistance to movement than the controlled digit, and decreasing the force applied to rotate the controlled digit when the controlling digit experiences a lesser resistance to movement than the controlled digit.

As for the mechanism discussed above, this method allows the digits to be controlled for an adaptive grip with only a single actuator at the palm unit applying a single force to the digit mechanism. The method may include using any or all features discussed above in relation to the first aspect and preferred/optional features thereof In order to generate the required adaptive grip the force balancing mechanism mechanically adjusts the magnitude of the moment applied by the lower digit rotation mechanism and/or the upper digit rotation mechanism in accordance with the magnitude(s) of outside forces resisting rotation of the upper digit and/or the lower digit and as a result the two rotation mechanisms preferentially apply movement to the digit experiencing lower resistance to movement. This is achieved by increasing the force applied to rotate a controlled digit when a controlling digit experiences a greater resistance to movement than the controlled digit, and decreasing the force applied to rotate the controlled digit when the controlling digit experiences a lesser resistance to movement than the controlled digit. The controlling digit may be the upper digit and the controlled digit the lower digit, or vice versa.

The method may include using a clutch for transmission of a varying amount of power for rotation of the controlled digit, and controlling the clutch to adjust the varying amount of power in accordance with the degree of resistance to motion of the controlling digit.

The step of controlling the clutch may be done using a mechanical device that is moved in accordance with the magnitude of the resistance to movement of the controlling digit, for example a lever device as discussed above, preferably combined with using a band brake as the clutch.

Preferred features of each aspect of the invention may be combined with the other aspects of the invention, and optionally with preferred features of the other aspects, as far as is applicable or appropriate.

Certain preferred embodiments of the invention will now be described by way of example only and with reference to the accompanying drawings in which.

By way of a preferred embodiment the drawings show a prosthetic hand and various features of the mechanisms used to produce finger and thumb movements for this prosthetic hand. It will however be appreciated that the same mechanisms could equally well be used in artificial hands for other purposes, for example for remote handling or in robotic applications. In addition, it will be noted that whilst there are particular advantages to the various features of the hand when taken in combination as shown in the Figures, there are also advantages that would arise when the different features of the hand are taken alone, for example the arrangement of the finger joint as described herein would provide advantages when used with alternative driving mechanisms and not just the hydraulic driving mechanism with the particular arrangement of the current palm unit, and similarly the palm unit and/or hydraulic circuit described herein would provide advantages when used with an alternative arrangement for the finger and thumb mechanisms.

Figure 1:
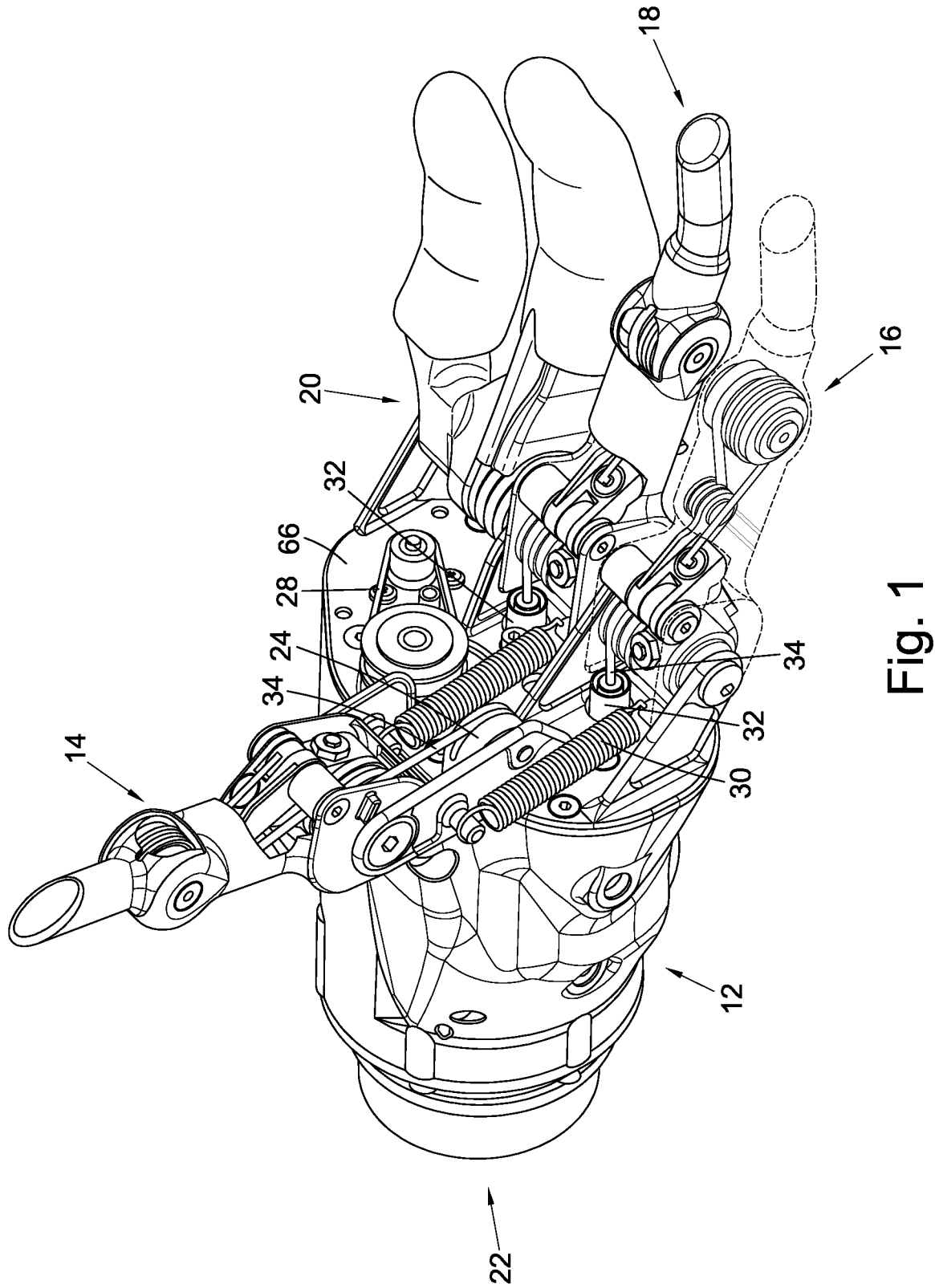
FIG. 1 shows a design for a prosthetic hand in perspective view with the cosmetic glove removed and one finger shown partially transparent so that internal detail can be seen.
Figure 2:
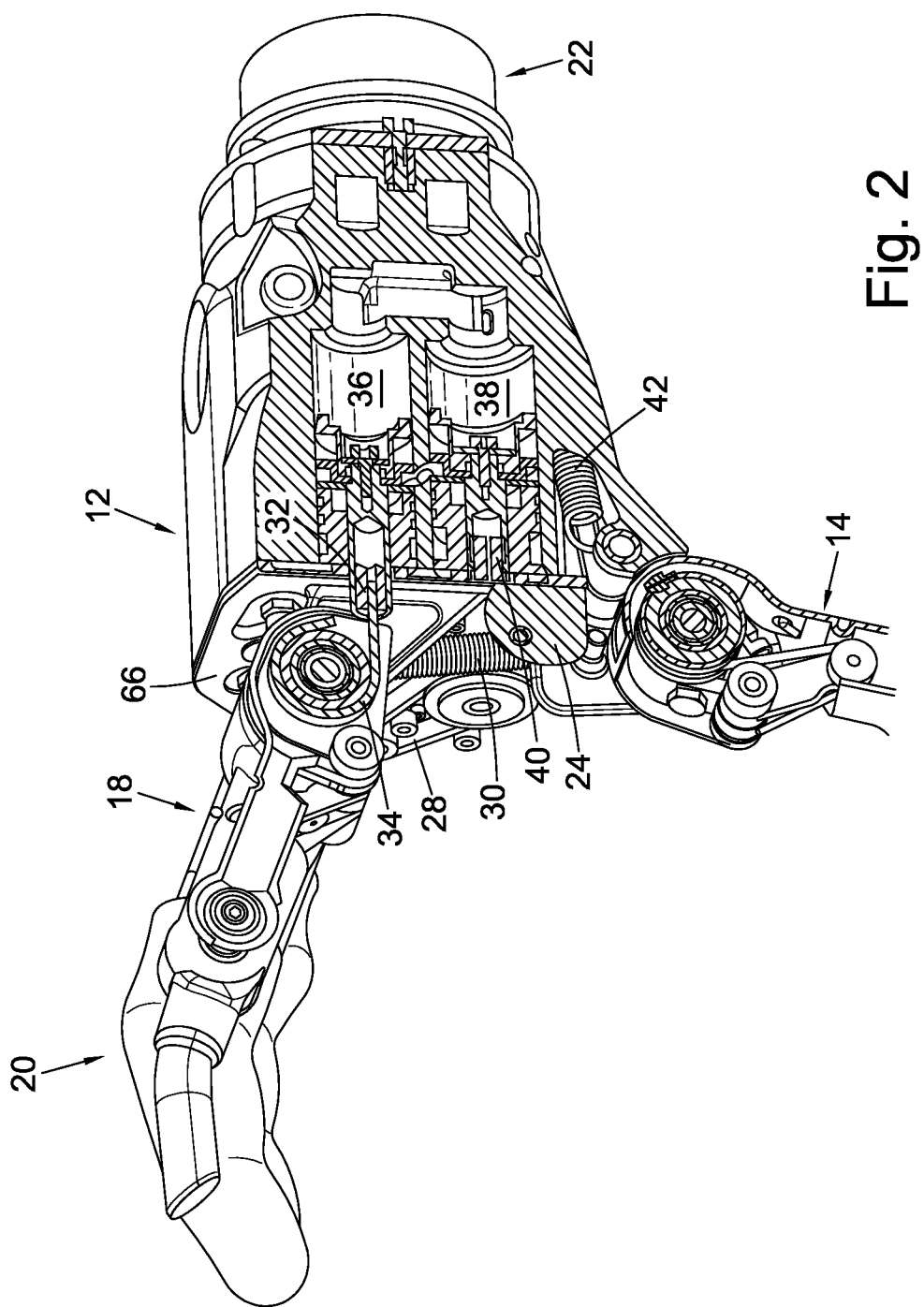
FIG. 2 is a partial cutaway view of the prosthetic hand of FIG. 1 showing a cross-section through the hydraulic cylinders for the middle finger and for the thumb.

Considering the Figures in more detail, FIG. 1 shows a perspective view for a prosthetic hand including a palm unit 12 a thumb mechanism 14, an index finger mechanism 16, a middle finger mechanism 18 and a combined ring finger/little finger mechanism 20. FIG. 2 shows a partial cutaway view with a slice taken along the line of the thumb 14 and between the index finger 16 and middle finger 18.

In this example the hand is provided with a standard quick connect Otto Bock design wrist joint 22 that allows for coupling with batteries and one or two electromyocardiographic (EMG) sensors, which would typically be mounted inside the user's underarm. It would of course be possible to adapt the hand to use an alternative wrist connection system if required. Advantageously, the coupling for the wrist joint 22 is 3-D printed. The use of a standard quick connect system 22 makes it possible for an existing electric hand prosthetic user to try this hand very easily.

The index finger mechanism 16 and the middle finger mechanism 18 are very similar and differ generally only in relation to the size of the fingers. The thumb mechanism 14 is similar to the finger mechanisms 16, 18 with the addition of a pulley/guide 24 directing the main cable 34 about an angle to allow for the thumb 14 to open at 90° to the fingers 16, 18, 20, and of course with some changes in size and dimensions so as to accurately mimic typical dimensions for a thumb. The ring finger/little finger mechanism 20 is resiliently coupled to and effectively slaved with the mechanism for the first digit of the middle finger mechanism 18. In this example a coiled spring is used, and this is advantageously fitted with a bushing allowing for a sprung movement of the little and ring fingers whilst opening, within limits, and a free movement (resisted by the spring, but without any restriction on the extent of movement) in the closing direction.

Microprocessor control electronics and software are provided to interpret the signals from the user's EMG sensors. These electronics are mounted behind the quick connect 22 inside the palm unit 12, i.e. within the right hand side of the palm unit 12 when viewed in the orientation of FIG. 2. It is important to understand that this hand design can operate with just a single sensor input if necessary, and based solely on the "strength" of this signal it is possible to achieve a very adaptable grip controlled by the user, as explained in more detail below. The use of a second EMG sensor is preferred since it allows for a more intuitive action of the user in releasing the grip of the device: one sensor can be used to control closing of the hand, and the other sensor will control opening of the hand. However, if necessary a single sensor can be used along with a prearranged signal for switching from closing to opening of the hand, for example a "double click" type movement. Further detail of the construction and operation of the thumb and finger mechanisms 14, 16, 18 will be discussed below with reference to FIG. 3 and FIG. 4 and the relevant reference numerals are not shown in FIG. 1 and FIG. 2 for the sake of clarity. In FIGS. 1 and 2 further detail of the basic parts of the palm unit 12 can be seen including the belt 28 that couples the motor 68 to the hydraulic pumps (shown in further detail in FIG. 5 and FIG. 6 amongst others); finger return springs 30, which are connected at the base of the finger joints and urge the hand toward an open configuration; finger piston couplings 32, which join the finger main cables 34 to the finger hydraulic cylinders 36; the finger hydraulic cylinder 36 for the middle finger mechanism 18 (in cross-section in FIG. 2); the thumb hydraulic cylinder 38 (again in cross-section in FIG. 2) and thumb piston coupling 40; and the thumb return spring 42. The operation and interaction of these various features will be obtained from the discussion below and from the drawings.

Figure 3:
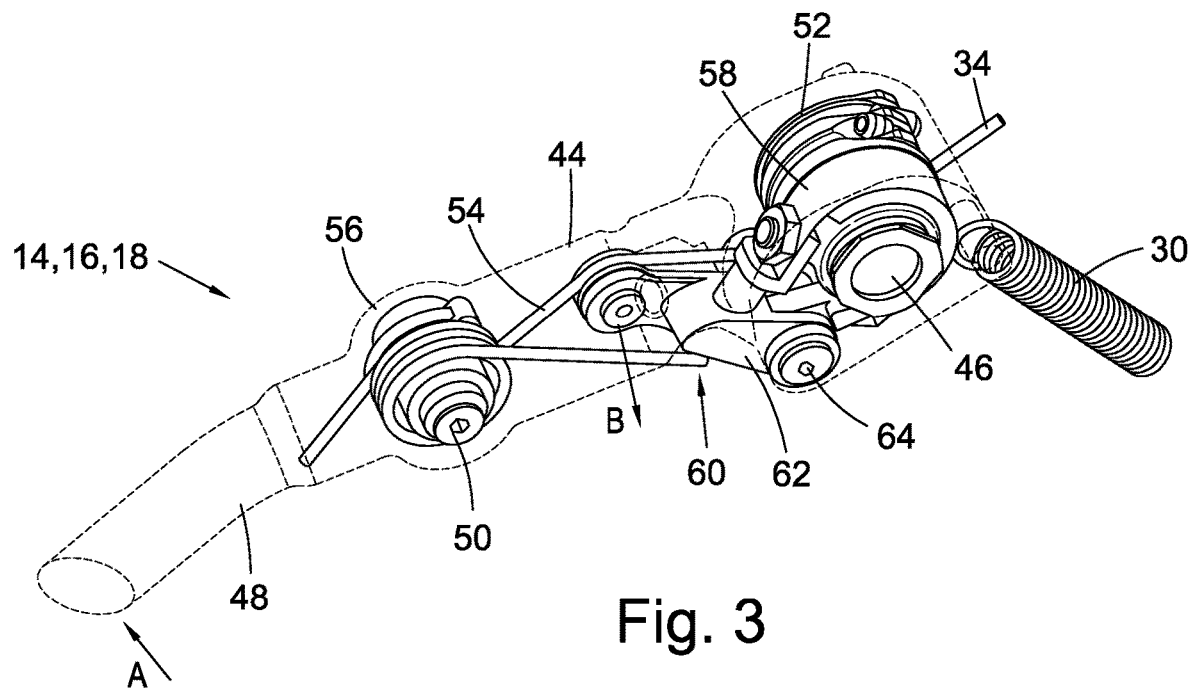
FIG. 3 shows a finger mechanism in more detail illustrating a clutch system for producing adaptive movement with the finger joints.
Figure 4:
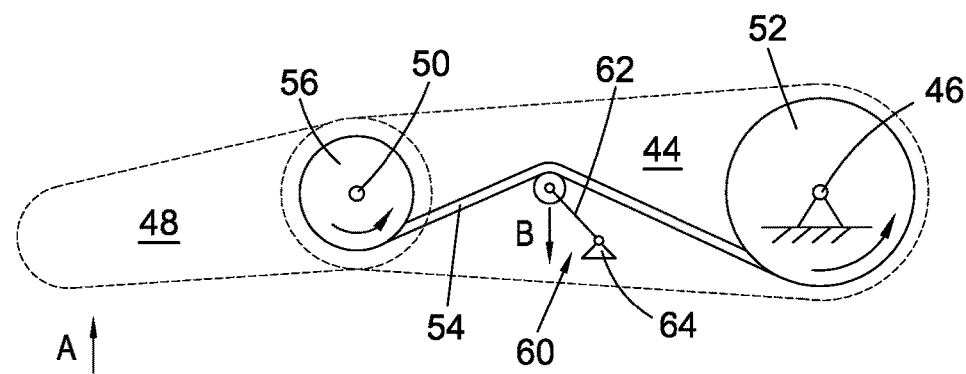
FIG. 4 is a schematic diagram showing the basic principles of operation of the clutch system.

Turning now to FIGS. 3 and 4, which show a finger mechanism in greater detail, it should first be noted that the same basic functional parts are used for both the index finger mechanism 16 and middle finger mechanism 18, as well as also for the thumb mechanism 14, with appropriate adjustments to achieve the required difference in size for the different fingers and the thumb. Thus, in the discussion below references to the fingers and finger joints can be taken to apply equally well to the thumb and thumb joints.

In this explanation the upper digit is the digit of the finger or thumb at the distal end, i.e. closest to the fingertip, and the lower digit is the digit of the finger or thumb at the proximal end, i.e. closest to the palm, and the terms upper and lower are used in the same way to refer to other parts of the mechanism. This example uses two digits for each of the index finger and middle finger mechanisms 16, 18 and for the thumb mechanism 14. It would be possible to expand to have three digits by repeating the mechanism described below for a third joint of the finger and to thereby obtain an even more natural finger movement. However, this is considered to add additional complexity without any significant benefit in relation to usability and the grip patterns that can be achieved.

FIG. 3 shows detail of a finger joint with the outer housing shown transparent so that the internal mechanism can be understood. FIG. 4 shows a part of the mechanism in schematic form, with equivalent parts given the same reference numbers.

A lower digit 44 is connected to the palm unit 12 (not shown in these Figures) via a pivot along a lower axis of rotation 46. The finger return spring 30 is positioned so as to urge the lower digit 44 back towards the open position, rotating it around the lower axis of rotation 46. At the distal end of the lower digit 44 and upper digit 48 is connected and can rotate relative to the lower digit 44 via a pivot along an upper axis of rotation 50. The finger main cable 34 is attached to a lower pulley 52 placed on the lower axis of rotation 46 and tension on the finger main cable 34 will rotate the lower pulley 52 in order to rotate the finger towards a closed position, with an adaptive grip as discussed below. In the view in FIGS. 3 and 4 shown this rotation would be in an anticlockwise direction.

It is important to allow for rotation of both the upper digit 48 and the lower digit 44, and advantageously this is done in such a way so as to provide an adaptive grip that can react to pressure on either one of the digits 44, 48. This is in contrast to various prior art arrangements that have a fixed mechanical relationship between the various digits in finger joint, requiring that the upper digit rotate in proportion to rotation of the lower digit. With the current design when the finger main cable 34 is pulled by the actuating mechanism (the piston connector of the finger hydraulic cylinder in this example) then this rotates the lower pulley 52 which applies tension to a secondary cable 54 that is connected to an upper pulley 56. The upper pulley 56 is mounted on the upper axis of rotation 50 and arranged such that rotation of the upper pulley will rotate the upper digit 48, pulling it toward the closed position (again, an anticlockwise rotation in the orientation shown in the Figures).

In order to achieve the required adaptive grip the current joint design uses a brake/clutch arrangement 58 to transfer rotational forces from the lower pulley 52 to the lower joint 44 in accordance with the tension in the secondary cable 54. The brake/clutch arrangement 58 allows for a degree of slipping in the system, so that either one digit can rotate whilst the other digit has stopped moving. The strength of the forces applied via brake/clutch arrangement 58 varies dependent on the balance of forces on the digits. Thus, in situations where there is less resistance to the closing motion of the upper digit 48 then there will be a reduced force closing the lower digit 44, whereas when there is increased resistance to the closing motion of the upper digit 48 then there will be an increased force closing the lower digit 44. The brake/clutch arrangement 52 and the various pulleys are arranged so that if there is no resistance to closing motion of the upper digit 48 or lower digit 44 then both digits will pull close with a similar degree of rotational motion resulting in a pincer grip pattern. However, when any one digit meets with resistance, i.e. when it contacts an object that is to be gripped, then its movement is stopped and forces are transferred preferentially to the other digit of that finger joint, which will continue to move until it meets with a similar resistance. When all of the digits are in contact with an object then the pressure will increase and therefore the strength of grip will also increase. The mechanism hence balances torques between the upper digit 48 and lower digit 44 ensuring that each finger mechanism 16, 18 (and likewise the thumb mechanism 14) provides an intuitive adaptive grip with a great flexibility in the grip pattern that can be achieved, whilst only requiring a single actuator input in the form of tension on the main cable 34.

In this example the brake/clutch arrangement 58 is a band brake. It will, however, be apparent that this band brake could be replaced by alternative designs for a brake/clutch arrangement 58, such as a system using clutch plates. The brake/clutch arrangement 58 is coupled to a torque balancing mechanism 60 that arranged so that as the tension in the secondary cable 54 increases then the brake/clutch arrangement 58 transfers increased forces between the lower pulley 52 and the lower digit 44. In this example the torque balancing mechanism 60 comprises a lever arm 62 attached to a pivot 64 that is fixed relative to the lower axis of rotation 46 and fixed relative to the main body of the lower digit 44. This is shown schematically in FIG. 4. The end of the lever arm 62 presses against the secondary cable 54, with the secondary cable 54 going through a change in direction around a guide surface at the end of the lever arm 62, such that tension in the secondary cable 54 will generate a force pushing the end of the lever arm 62.

When the lower pulley 52 is pulled by the main cable 34 (not shown in FIG. 4) and rotates in the anticlockwise direction then tension is applied along the secondary cable 54 and the upper pulley 56 also tends to rotate in an anticlockwise direction. As noted above, with no resistance to motion then the brake/clutch arrangement 58 is set so that both the lower digit 44 and the upper digit 48 both rotate to form a pincer grip pattern. If there is resistance to motion of the upper digit 48, for example through a contact force applied with the direction A at the fingertip, then the tension in the secondary cable 54 would increase. As will be understood from FIG. 4 this increased tension will have the effect of pushing the end of the lever arm 62 with a greater force in the direction B, hence applying a moment to the lever arm 62 around its pivot 64.

FIG. 3 shows further detail of the connections between the lever arm 62 and the brake/clutch arrangement 58, i.e. the band brake in this example. Movement of the lever arm 62 increases forces on the band brake thereby increasing transfer of forces between the lower pulley 52 and the lower digit 44, creating a tendency for the lower digit 44 to be closed in preference to closing of the upper digit 48. If there were also resistance to movement of the lower digit 44 then increasing resistance of this type would result eventually in balancing of the forces as pressure increased via the main cable 34, so that both digits will apply pressure to increase the strength of the grip when there is full contact of both digits with an object. If there is resistance to motion of the lower digit 44 with less resistance to motion of the upper digit 48 then the lower digit 44 will cease to rotate and the upper digit 48 will continue to rotate, with a high degree of slipping of the brake/clutch arrangement 58 which at this point would be transferring relatively low forces between the lower pulley 52 and the lower digit 44. The mechanism described above therefore provides the required intuitive and adaptive movement of each of the finger and thumb mechanisms 14, 16, 18.

Figure 10:
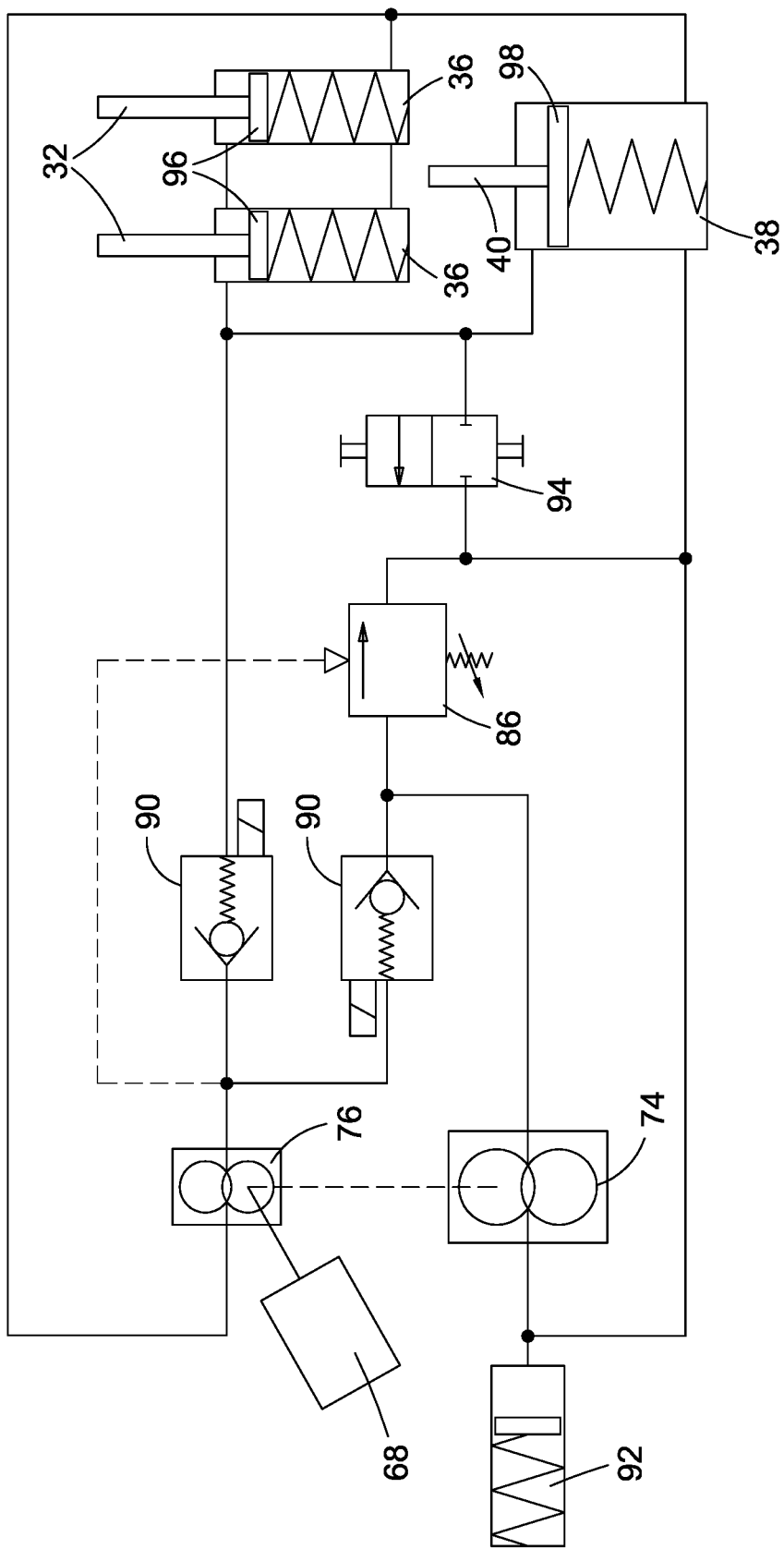
FIG. 10 is a hydraulic schematic.
Figure 11:
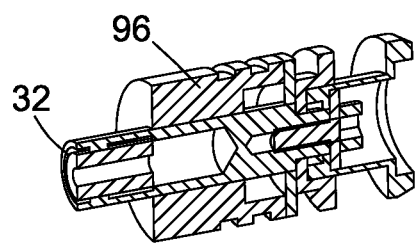
FIGS. 11 and 12 show a cross-section and perspective view of a hydraulic cylinder for the index and middle fingers.
Figure 12:
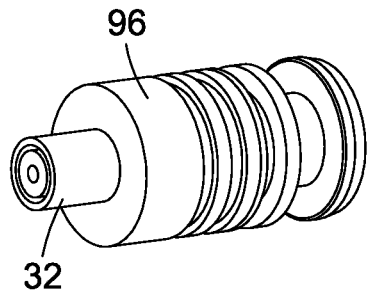
Figure 13:
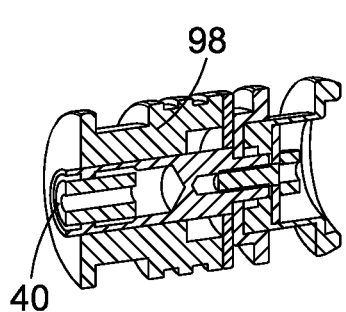
FIGS. 13 and 14 shows similar views for a hydraulic cylinder for the thumb.
Figure 14:
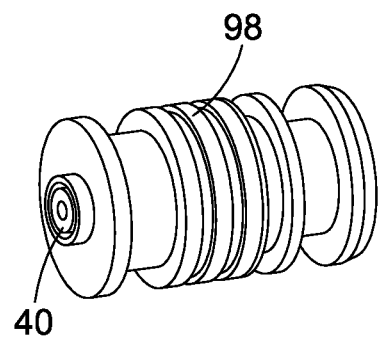

Further adaptability of the grip pattern provided by the hand comes from the fact that the two finger hydraulic cylinders 36 and the thumb hydraulic cylinder 38 are coupled together with equal pressure, as can be seen in the cross-section drawing in FIG. 2 and the hydraulic schematic of FIG. 10, for example. As a result then as well as a resistance on individual digits affecting the pattern with which an individual finger or thumb mechanism closes, then varying resistance between the different finger and thumb mechanisms 14, 16, 18, 20 will result in the hand closing in a natural fashion around a gripped object of any shape. The first finger or thumb to meet the object (with all digits) will cease moving and the hydraulic interconnection means that fluid will continue, without an increase in hydraulic pressure, to move the digits of the other finger(s) and/or the thumb until all digits of all the finger and thumb mechanisms are meeting similar resistance, at which point the hydraulic pressure will increase and the strength of grip of the whole hand increases.

As mentioned above, movement of the fingers is controlled via one or two EMG sensors controlling a variable speed motor that drives the hydraulic pumps of the system. The hydraulic circuit and its interaction with the variable speed motor are explained in more detail below. In relation to the grip from each finger, what is important is that the user can choose when to close the hand and when to open the hand, and the digits in each finger will grip adaptively as explained above. Therefore, the user is able to stop movement in order to acquire the desired grip, and the user can also place the hand against an object or use their other hand in order to resist movement of the fingers/thumb and therefore close the hand with the fingers and thumb in a required pattern. Unlike many of the prior art systems there is no requirement for a complicated code system requiring a sequence of "clicks" of an EMG sensor in order to place the hand into a required grip pattern. Instead, it will adaptively grip to any object that is presented to it, and also by means of selectively resisting motion of digits as required the user can place the hand into any pattern that they require.

The speed and direction of movement of the fingers and thumb is controlled by the speed and direction of the electric motor. The pressure applied is controlled by two hydraulic pumps as discussed below, with a hydraulic circuit that switches automatically between a low pressure high-volume configuration and a high-pressure low-volume configuration. The control of the fingers by the speed and direction of the electric motor is different to "normal" hydraulics where the electric motor runs at a continuous speed in a single direction and multiple valves are used to control the speed and direction of the flow of hydraulic fluid. Controlling both speed and direction of the hydraulic actuators with the electric motor minimises the number of valves required. This makes the hydraulic system much simpler and results in the hydraulic circuit operating in a considerably different way to "normal" hydraulics. This type of system is only feasible in hydraulic systems with relatively low pressures and small fluid volumes, which works well for an artificial hand, but would not be applicable in all other fields where hydraulics are used.

Since the fingers and thumb are robustly actuated via hydraulics and are spring return then they can be pushed away from their natural position without risk of damaging the mechanism. In particular, the fingers are able to absorb knocks and other intended or inadvertent impacts by moving against the hydraulics and the springs without risk of damage to the mechanism of the hand. This is a significant advantage compared to some prior art products that use lead screws, worm gears, and so on, which are very fragile and vulnerable to damage when the fingers or thumb are knocked.

To provide the required strength and lightness whilst also achieving the complex shapes necessary then 3-D printing is used in manufacturing the device. The outer bodies for the upper and lower digits of the fingers and thumb mechanisms 14, 16, 18 are 3-D printed in titanium, as is the structural end plate 66 of the palm unit 12. The main body for the palm unit 12, which is described in more detail below, is in this example 3-D printed in plastics, but could be re-engineered to be printed in aluminium or titanium with adjustments to the design for maximum weight saving (for example, by including additional voids such as in a honeycomb type construction). The various cables are made of steel in this example.

As well as providing advantages resulting from the arrangement of the finger and thumb mechanisms 14, 16, 18 as described above, the artificial hand of FIG. 1 also has important and advantageous features in relation to the arrangement of the palm unit 12 and the internal parts thereof. FIGS. 5 to 9 illustrate additional details of these parts, which are also described below. FIG. 10 is hydraulic schematic for the palm unit 12 illustrating the arrangement of the high and low pressure hydraulic pumps and the simplicity of the hydraulic circuit (especially as compared to prior art systems which are fully hydraulic such as the "Fluidhand" design). FIGS. 11 to 26 show various components of the system in greater detail.

Figure 5:
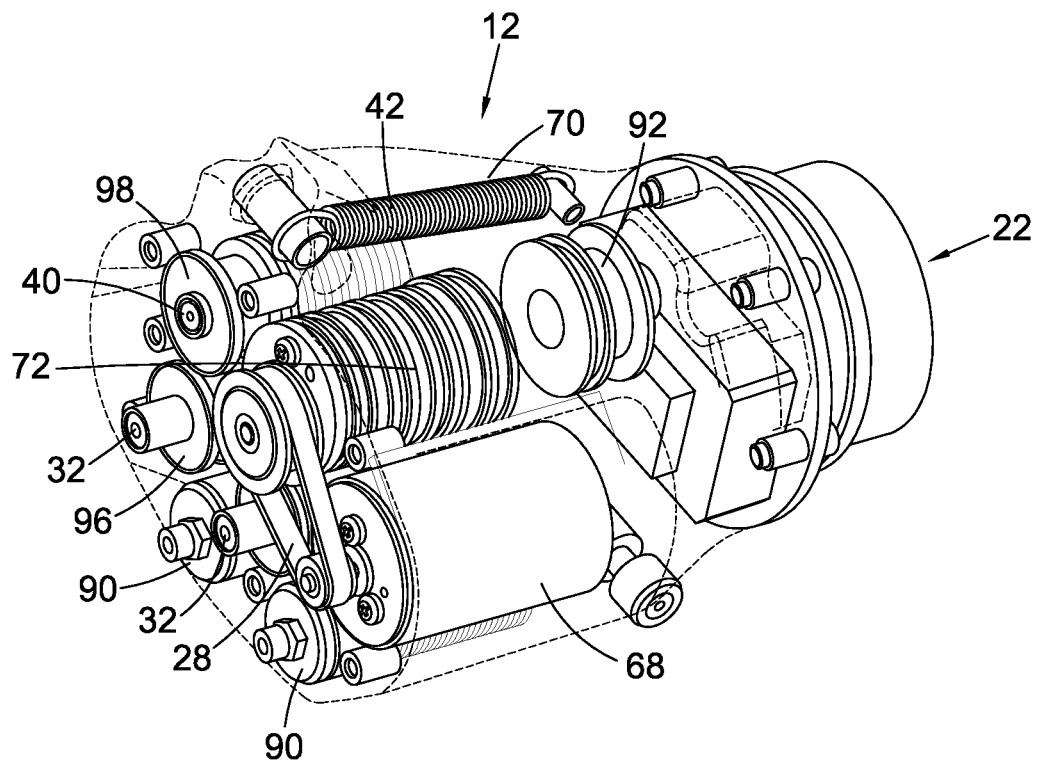
FIG. 5 is a perspective view of the palm unit with the outer housing shown transparent so that internal detail of the motor and hydraulic pumps can be seen.

It will be seen from the FIG. 5 that all the hydraulic elements as well as an electric motor 68 are fully contained within the palm unit 12, and they are housed in a palm unit body 70, the details of which can be seen in several of the Figures. The palm unit body 70 is shown without any other parts in FIG. 25, and without any other parts and with a cutaway section in FIG. 26. As noted above, the palm unit body 70 is 3-D printed out of plastics. In FIG. 5 the structural end plate 66 of the palm unit is removed so that the various connections can be seen in more detail, and the main body 70 is shown transparent for the same reason.

The electric motor 68 has an axis running lengthways along the palm unit 12 (from the wrist end toward the finger end) and this axis is parallel to the axis of a shaft that powers the hydraulic pump assembly 72. The electric motor 68 is coupled to the shaft of the hydraulic pump assembly 72 via a belt 28 that is located outside of the main body 70 of the palm unit 12 allowing better access for assembly and for maintenance. The electric motor 68 and the hydraulic pump assembly 72 are placed on the side of the hand opposite to the thumb. Finger piston couplings 32 and the thumb piston coupling 40 extend from the end of the palm unit body 70 from their respective hydraulic cylinders 36, 38 which extend back into the palm unit body 17 and are also parallel with the axis of the motor along the length of the palm unit 12. Also visible in FIG. 5 are the ends of two electromagnet controlled valves 90, and these are described in further detail below with reference to FIG. 10 as well as FIGS. 23 and 24.

Figure 6:
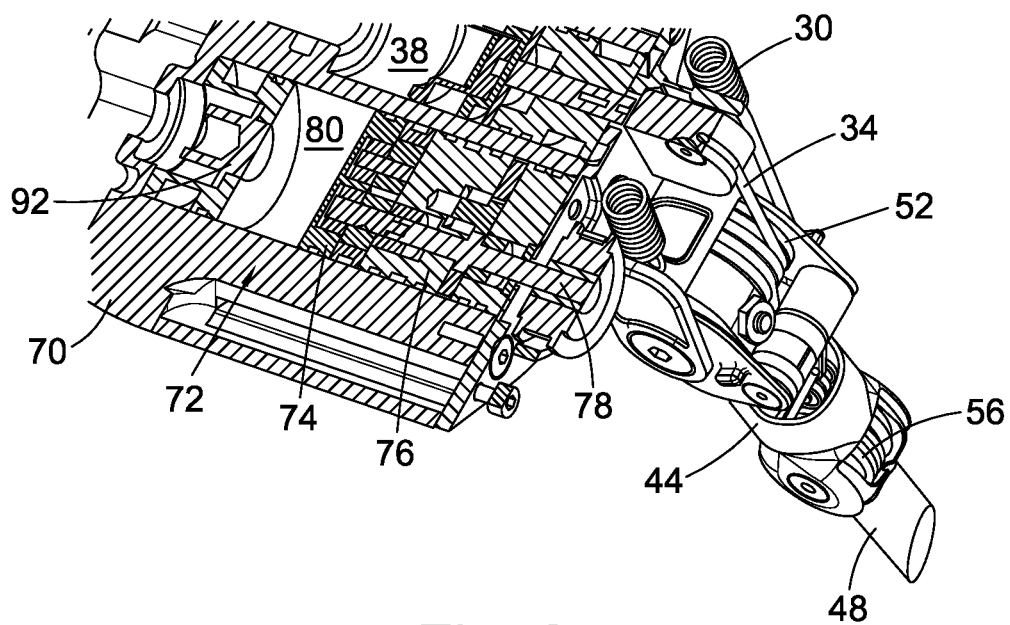
FIG. 6 is a partial cross-section through the palm unit showing the high and low pressure hydraulic pump and equaliser adjacent to the hydraulic cylinder for the thumb.
Figure 7:
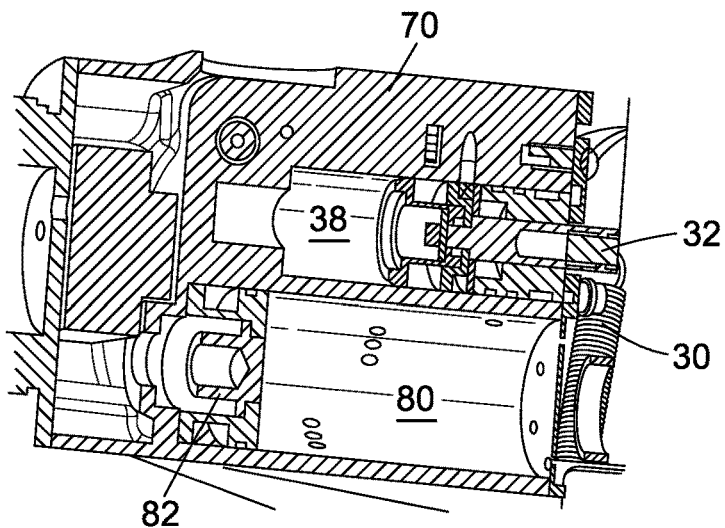
FIG. 7 shows a similar cross-section to FIG. 6, from a different angle, with the hydraulic pump assembly removed so that the hydraulic pump pressure and suction channels can be seen.
Figures 17, 18:
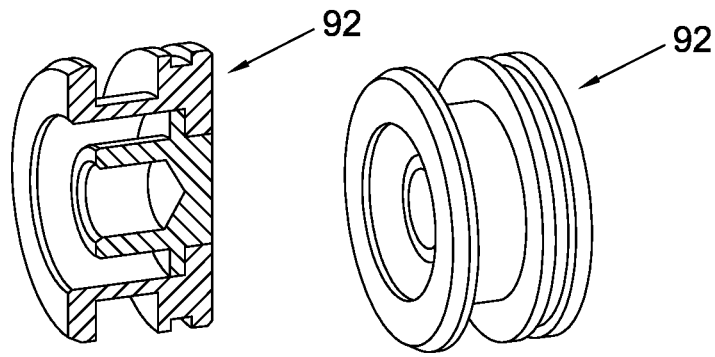
FIGS. 17 and 18 show more detail of an equaliser that is seen in situ in FIG. 5 and FIG. 6.

Details of the palm unit can be seen in cross-section in FIG. 6 and FIG. 7, particular for the hydraulic pump assembly 72 and also, in part, hydraulic connection passages and the thumb hydraulic cylinder 38. The hydraulic pump assembly 72 includes both a low-pressure, high-volume, hydraulic pump 74 and a high-pressure, low-volume, hydraulic pump 76, which receive power from the same shaft 78, turned by the motor 68. The interaction of the two hydraulic pumps 74, 76 with the hydraulic circuit will be explained below in connection with FIG. 10. The shaft 78 passes through the high-pressure hydraulic pump 76 to the low-pressure hydraulic pump 74 and operates both hydraulic pumps 74, 76 simultaneously. The hydraulic pumps 74, 76 are functionally separate, but they are formed as a single assembly with a common shaft for ease of manufacture and assembly. This also saves weight and space as well as allowing the two hydraulic pumps 74, 76 to be mounted within a single chamber 80 within the palm unit body 70. Beyond the low pressure hydraulic pump 74, and in the same chamber 80 of the palm unit body 70 an equaliser 92 is installed. FIGS. 17 and 18 provide a close-up view of the equaliser 92. The equaliser 92 operates via spring and generates a positive oil pressure on the suction side of the low and high pressure hydraulic pumps 74, 76. The equaliser 92 acts to prevent cavitation in the hydraulic pumps 74, 76. The equaliser also moves to adjust the available volume of the chamber 80 to compensate for movement of the cylinder rods for the finger and thumb hydraulic cylinders 36, 38, which would otherwise result in changes in the volume of the system.

Figure 26:
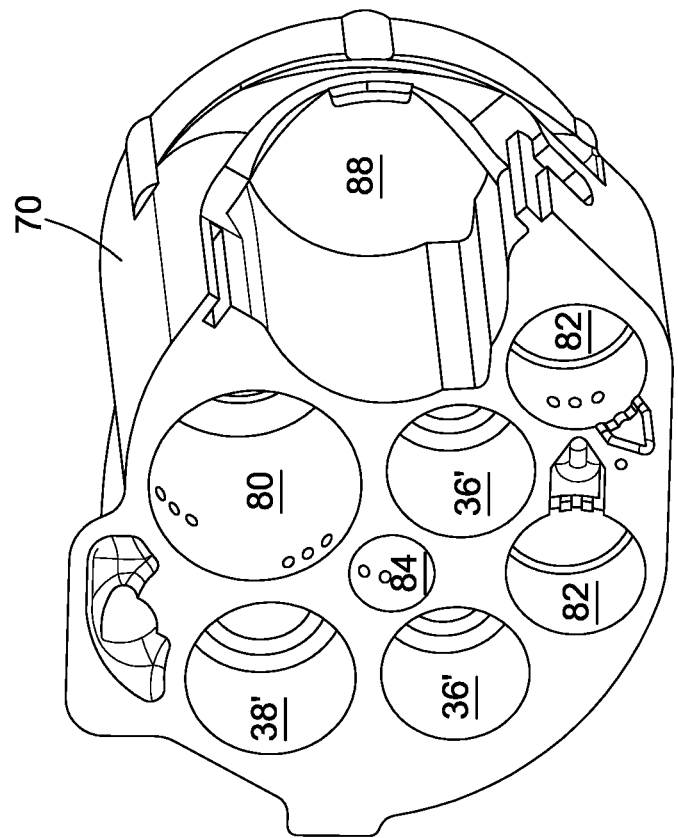
FIG. 26 shows a cutaway view of the body section illustrating some of the hydraulic connections.
Figure 25:
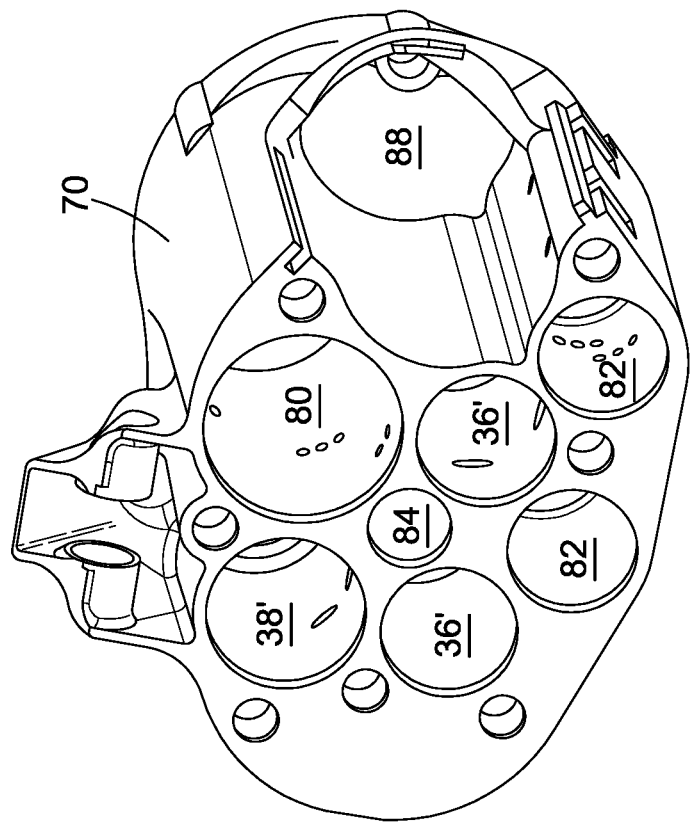
FIG. 25 shows a 3-D printed body section for the hydraulic subassembly shown in FIG. 8.

Referring again to FIGS. 25 and 26 it will be seen that as well as the hydraulic pump and equaliser chamber 80 the palm unit body 70 also includes three hydraulic chambers 36', 38' to form the hydraulic cylinders 36, 38 for the thumb and two finger mechanisms, two valve openings 82 for receiving the electromagnet controlled valves 90, a valve opening 84 for receiving a pressure controlled valve 86 (not visible in FIG. 5, discussed in more detail below with reference to FIGS. 21 and 22) and a motor chamber 88 for holding the motor 68. The partially cutaway view in FIG. 26 shows an example of how the hydraulic circuit is formed as an integral part of the palm unit body 70. All the required interconnections between the various hydraulic chambers are formed as passages between chambers in a single unit. The use of 3-D printing for the palm unit body 70 enables this complicated shape to be formed without undue expense. Since all significant forces on the palm unit body are axial than a relatively soft plastics material can be used, with relatively thin sections between the various axial components. The pressure of the hydraulic fluid within the cylinders creates radial forces, but these forces act generally symmetrically and the circular shapes used are effecting in containing these pressures even with relatively weak plastic materials. Although these thin sections would otherwise be vulnerable to flexing as there are no radial forces then this is not a particular risk for the system. This arrangement also provides the advantage that all of the hydraulic circuit is contained within a single housing 70 and can therefore easily be kept fully sealed. The proposed palm unit 12 hence presents minimal risk of hydraulic leakage with increased robustness compared to prior art designs using hydraulic actuation for artificial hands.

Both of the suction and pressure sides of the two hydraulic pumps 74, 76 are within the palm unit and connect to various channels through the palm unit body 70 that form the hydraulic circuit of FIG. 10. Oil (or another working fluid) is thus transported from the hydraulic pumps 74, 76 to the valves without passing outside of the palm unit body 70. The suction and pressure sides of the hydraulic pumps 74, 76 are separated from the outside world and all of the hydraulics using O-ring seals. As the hydraulic pumps 74, 76 are isolated from the outside world in this way then there is no need for any hydraulic seals between the hydraulic pump plates. This is because any leakage will only be internal and can to some extent be disregarded. Avoiding the use of hydraulic pump plate seals save space and enables easier faster and cheaper manufacture of the hydraulic pump assembly 72.

Figure 8:
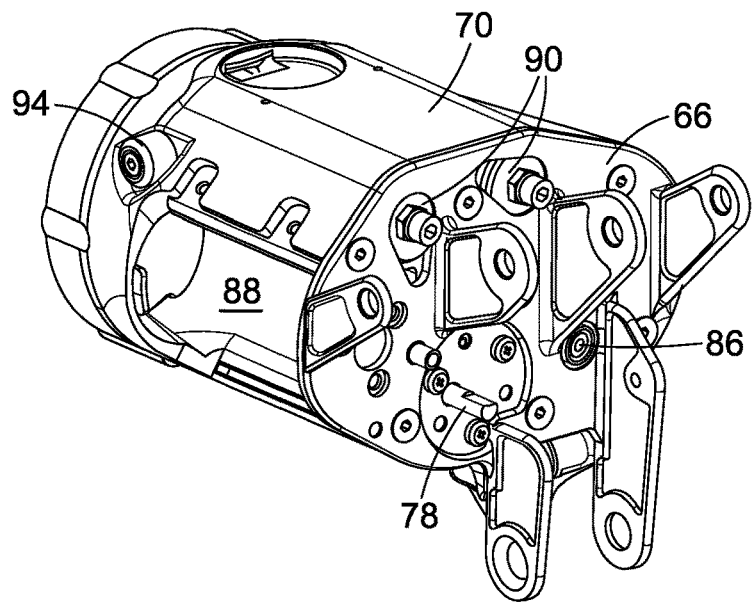
FIG. 8 is a perspective view of a hydraulic subassembly of the palm unit with the finger joints at the upper part and the thumb joint at the lower part and also showing the location of an emergency hydraulic valve.
Figure 9:
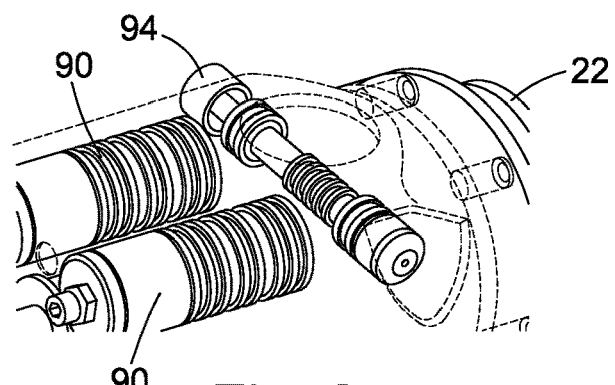
FIG. 9 shows the emergency valve in more detail with the outer part of the hydraulic subassembly shown transparent for clarity.

The other hydraulic parts can similarly easily be isolated from the outside world by O-rings or similar seals. This makes the whole hydraulic system very robust and easy to assemble and maintain. Since the hydraulic cylinders 36, 38 are also formed as a part of the palm unit body 70 then they do not move or rotate with the moving parts and consequently they can receive hydraulic fluid from fixed channels within the palm unit body 70. Each hydraulic part can be individually removed and replaced for maintenance or repair work. There is also an easily isolated hydraulic subassembly formed by the palm unit body 70 enclosing the various hydraulic parts and optionally including the structural end plate 66. An orthopaedic workshop could choose to do maintenance in-house, or they could choose to remove the fingers and wrist connector along with the motor and send the hydraulic subassembly back to the manufacturer for maintenance or repairs. The hydraulic subassembly is shown in FIG. 8. As well as the various parts that have already been introduced the hydraulic subassembly also includes an emergency release valve 94, which can be seen in further detail in FIG. 9 and is shown in isolation in FIG. 15 and FIG. 16.

Figure 15:
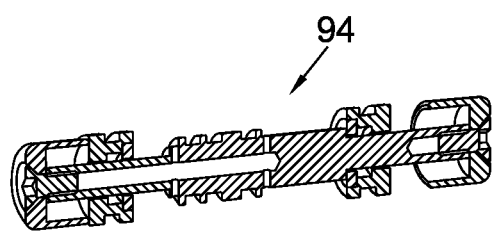
FIGS. 15 and 16 show the emergency valve in cross-section and perspective view.
Figure 16:
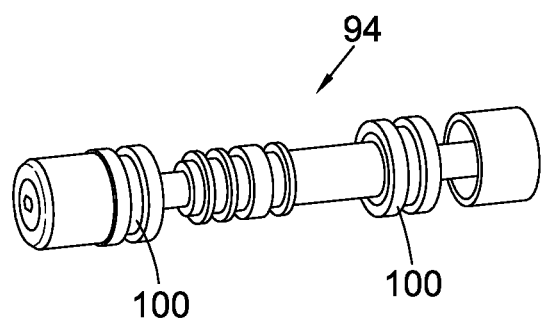

The emergency valve 94 is a mechanical user controlled valve that can be opened in case of any mechanical, hydraulic or electronic failure in order to release the hydraulic pressure in the system. The valve bypasses the electrically controlled valves 80 and connects the pressure sides of the thumb and fingers cylinders 36, 38 directly to the equaliser 92. Since there is a spring return then the hand will automatically move to open configuration when the emergency valve is pushed, but no hydraulic fluid is released from the system. FIGS. 15 and 16 show the emergency valve in more detail. Mounting and sealing rings 100 are fixed in place within the palm unit body 70 and the main shaft of the valve can be slid relative to these rings 100 in order to release the pressure from the system if required by the user.

FIG. 10 shows the hydraulic schematic for the system. The basic connections will have been apparent from the discussion above. The motor 68 powers the high-volume low-pressure hydraulic pump 74 and the low-volume high-pressure hydraulic pump 76. The hydraulic pumps 74, 76 provide hydraulic fluid to the index and middle finger cylinders 36 and the thumb cylinder 38. The index and middle finger cylinders 36 have pistons 96 and piston connectors 32, which are coupled to the main cables 34 for the finger joints as shown in the preceding Figures. The thumb cylinder 38 has a piston 98 and piston connector 40, which is coupled to the main cable 34 for the thumb joint, again as shown in the preceding Figures. FIGS. 11 through 14 show close-up views in cross-section and perspective for the pistons 96, 98 and piston connectors 32, 40. It will be noted that the diameter of the thumb piston 98 (and cylinder 38) is slightly larger than the diameter of the index and middle finger piston 96 (and cylinders 36). This is in order to balance the forces between the thumb and two fingers when the tips of the fingers and thumb close into a pincer grip. The cylinders are spring return so that when the hydraulic pressure is released, i.e. when there is no differential in hydraulic pressure between the two sides of the cylinder across the piston, then the system will return to an at rest configuration when the hand is open. The equaliser 92 is connected to the suction side of the hydraulic pumps 74, 76 and has the function explained above.

Figure 19:
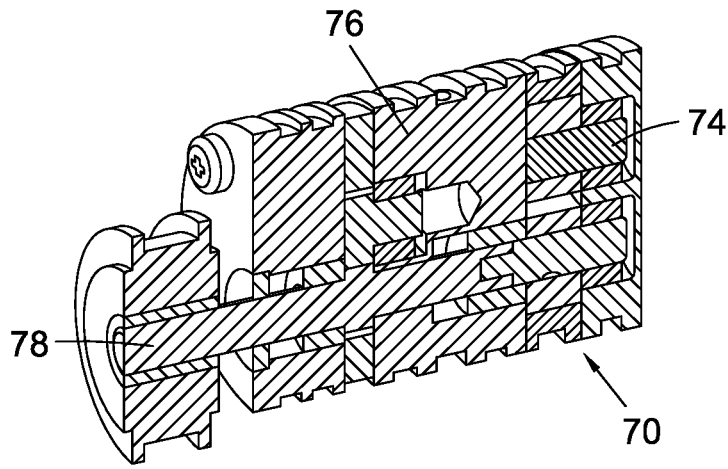
FIGS. 19 and 20 show a cross-section and perspective view for the high and low pressure hydraulic pumps, which again are already seen in situ in FIG. 5 and FIG. 6.
Figure 20:
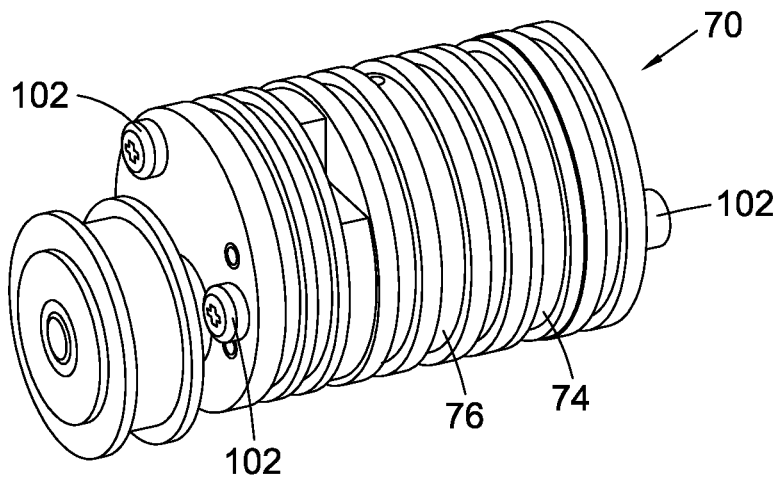

The arrangement of the hydraulic pump assembly 72 is shown in greater detail in FIG. 19 and FIG. 20. In this example the high-pressure hydraulic pump 76 is a gear pump using straight gears whereas the low pressure hydraulic pump 74 is a gear pump using helical gears. Helical gears dampen the sound from the hydraulic pump, which might otherwise be a problem for the low-pressure hydraulic pump 74. The high-pressure hydraulic pump 76 is assembled first, then the axle of the low-pressure hydraulic pump 74 is connected and the low-pressure hydraulic pump is assembled. The axle of the low-pressure hydraulic pump fits to the axle of the high-pressure hydraulic pump with axial play forming a single shaft 78 that powers both hydraulic pumps. The axial play is provided in order to keep the gears on each part of the hydraulic pumps' shaft axially independent of each other, ensuring that there is no interaction of the high and lower pressure parts of the hydraulic pump assembly during use.

All of the hydraulic pump plates are manufactured oversize, for example 1 mm in excess of the final size. The hydraulic pump plates are joined together by axial bolts 102 in order to form the hydraulic pump assembly 72. The hydraulic pump bolts 102 are tightened whilst the gears and shaft are being turned in order to allow for minimal tolerances between the gears and plates of the hydraulic pump and ensure that there is minimal play between gears and plates to thereby minimise the internal leakage. This allows for very little leakage despite the fact that hydraulic pump seals have been dispensed with as noted above. Once assembly is complete then the hydraulic pump assembly 72 is machined to the required final size and fitted with the required O-ring seals. This production method ensures that the hydraulic pump assembly 72 will always be the correct size for its chamber 80 in the hand palm and provides a cheap and quick way to produce the hydraulic pumps whilst guaranteeing high quality seals between the hydraulic pump and the outside world.

Figure 21:
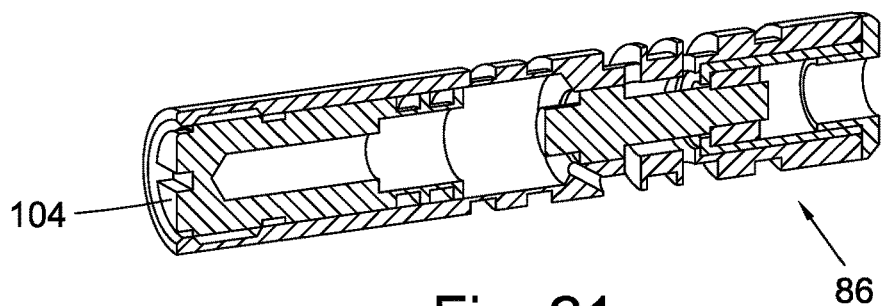
FIGS. 21 and 22 show a cross-section and perspective view for a pressure controlled valve that redirect the oil flow to switch from low-pressure to high pressure operation.
Figure 22:
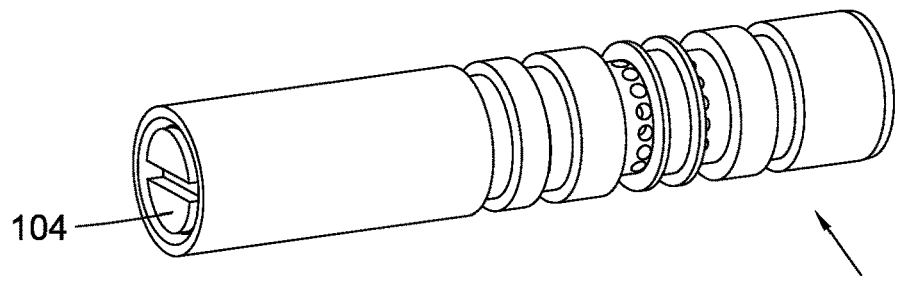

FIGS. 21 and 22 show the pressure controlled valve 86 that is used to switch between high and low pressure operation as described below. Typically the switching pressure would be set at between 10 to 15 bar, and this can be adjusted by a screw 104. When the preset pressure is reached then the valve switches position and flow of hydraulic fluid from the low-pressure hydraulic pump 74 is redirected as explained below.

Figure 23:
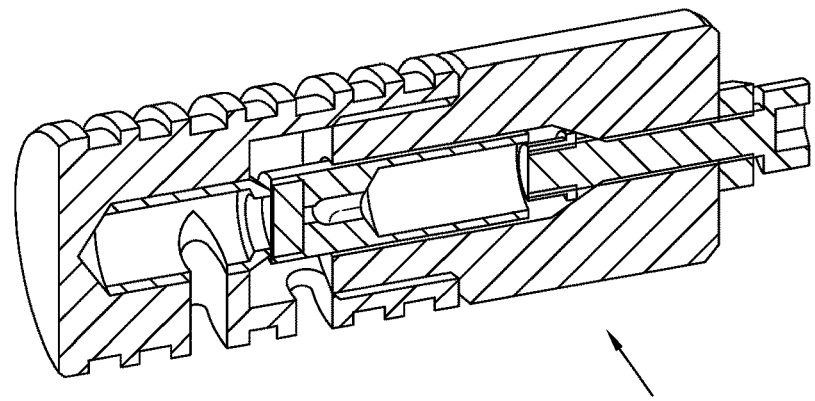
FIGS. 23 and 24 are a cross-section and perspective view of a design for an electromagnet controlled valve used within the hydraulic circuit.
Figure 24:
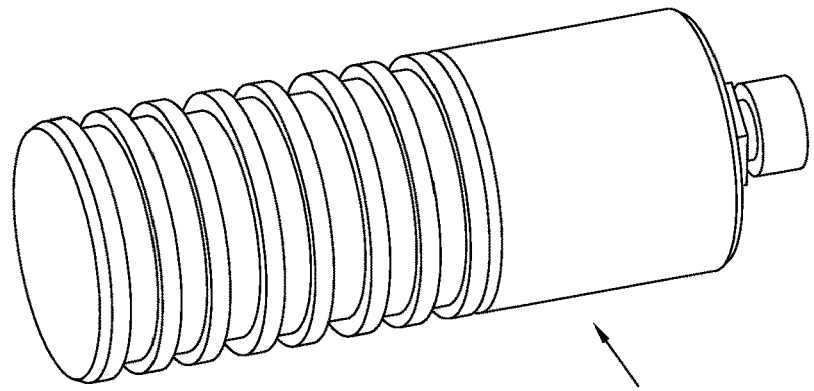

The other two valves of the system are electromagnet controlled valves 90 as shown in FIGS. 23 and 24. They operate as one-way valves and can be held in the open position via an electromagnet. One electromagnet controlled valve 90 is connected between the hydraulic pumps 74, 76 and the actuation cylinders 36, 38 for the fingers and the thumb and has the function of preventing hydraulic fluid from flowing out of the finger and thumb cylinders 36, 38 when the fingers are in the desired position. This valve hence acts as a finger locking valve 90 and makes sure that the motor 68 can be stopped without the risk of movement of the fingers away from the required position. Using a one-way hydraulic valve in this way saves battery life and means that there is no noise from the hand when the required finger position or grip of an object has been achieved.

The second electromagnet controlled valve 90 acts to close the channel between the high and low pressure hydraulic pumps 74, 76 when the system pressure increases over a set threshold and the pressure controlled valve 86 is opened. This valve 90 hence acts as a pressure retaining valve 90. Considering FIG. 10, it will be understood that during low-pressure operation both hydraulic pumps are connected to the cylinders 36, 38 and thus the high-volume low-pressure hydraulic pump 74 dominates leading to a fast movement of the pistons 96, 98 until there is resistance, for example as the fingers and thumb begin to grip an object. As described above the interconnection of the hydraulic cylinders and the design of the fingers to provide an adaptive grip means that the digits and fingers will move adaptively until there is resistance to motion of each part. When there is resistance to the movement of each part then the pressure in the system will begin to increase, increasing the grip strength from the hand. As the threshold value is reached then the pressure controlled valve 86 opens and the second electromagnet controlled valve 90 will close. At this time the high-pressure hydraulic pump 76 takes over and the system pressure can increase above the threshold, for example up to 50 bar, to further increase the grip strength. This combination of low and high pressure operation allows for an initial fast movement of the fingers with a low grip strength followed by the possibility of increasing the grip strength of the fingers to a significant degree using the high-pressure hydraulic pump 76. Whilst the pressure controlled valve 86 is opened the low-pressure hydraulic pump 74 continues to operate and simply re-circulates hydraulic fluid through the pressure controlled valve 86 back to the suction side of the low-pressure hydraulic pump 74.

This recirculation of hydraulic fluid from the low-pressure hydraulic pump 74 can easily be understood with reference again to FIG. 10. If the pressure controlled valve 86 is open and the lower electromagnet controlled valve 90 is closed then the low-pressure hydraulic pump 74 will recirculate fluid, without any pressure building up, around the lower loop of the system as shown in the Figure. When this is occurring then the high-pressure hydraulic pump 76 will be supplying low-volume high-pressure hydraulic fluid to the cylinders 38, 36 thereby allowing the increased strength of grip.

Also as seen in FIG. 10 the emergency valve 94 sits between the suction side of the hydraulic pumps 74, 76 and the cylinders 36, 38, and thus enables discharge of pressure from the cylinders in the event of any hydraulic or electrical failure, or other system failure.

As noted above, the motor 68 can be driven with varying speed in accordance with signals from the EMG sensor(s). In order to open the fingers the motor 68 is reversed. Thus, the user can easily control the speed of movement of the fingers both when opening and when closing the hand. Opening of the fingers will also occur naturally via the springs in the cylinders 36, 38 and the return springs 30, 70 mounted between the fingers and the palm unit 12. Since the fingers are locked in place by actuation of the electromagnetic valve 90 that forms the finger locking valve 90 then it is also necessary to have a small microprocessor routine to unlock the fingers and thereafter keep the finger locking valve 90 open so that the fingers can be opened (with the opening movement being controlled by the user as explained above). First the high-pressure hydraulic pump is operated forward in order to push the finger locking valve 90 open, and this valve can then be kept open by the electromagnet. The hydraulic pumps are stopped and then pressurised again at a lower pressure in order to allow the second electromagnet controlled valve 90, which is acting as a pressure retaining valve when in high-pressure operation, to be opened and again this is held open by the electromagnet. With both of the electromagnet controlled valves 90 being open then the hydraulic pumps can now be controlled with the motor running in reverse in order to open the hand. The unlocking action can be performed in a fraction of a second and is controlled by the microprocessor in response to a signal from the EMG sensor indicating that the user is trying to open the hand. Essentially, this process can be invisible to the user.

What is claimed is:

1. A digit mechanism for an artificial hand, the digit mechanism comprising:
   a lower digit arranged to be rotatably coupled to a palm unit of the artificial hand;
   an upper digit rotatably coupled to the lower digit;
   a lower digit rotation mechanism for applying a moment to the lower digit to rotate the lower digit relative to the palm unit;
   an upper digit rotation mechanism for applying a moment to the upper digit to rotate the upper digit relative to the lower digit; and
   a force balancing mechanism arranged so that if there is no resistance to closing motion of the upper digit or the lower digit then both digits will rotate about their respective rotation mechanisms at the same time, the force balancing mechanism providing mechanical adjustment of the magnitude of the moment applied by the lower digit rotation mechanism and/or the upper digit rotation mechanism in accordance with the magnitude(s) of outside forces resisting rotation of the upper digit and/or the lower digit in order to preferentially apply movement to the digit experiencing lower resistance to movement so that either digit is able to rotate whilst rotation of the other digit is stopped;
   wherein the force balancing mechanism is arranged to increase the force applied to rotate a controlled digit which is one of the upper digit or the lower digit when a controlling digit, which is the other of the upper digit or the lower digit experiences a greater resistance to movement than the controlled digit, and decrease the force applied to rotate the controlled digit when the controlling digit experiences a lesser resistance to movement than the controlled digit;
   wherein the lower digit rotation mechanism and upper digit rotation mechanism are arranged to be mechanically actuated, in use, by a force applied from a single actuator at the palm unit;
   wherein the force balancing mechanism includes a clutch for transmission of a varying amount of power for rotation of the controlled digit with the clutch being controlled to adjust the varying amount of power in accordance with the degree of resistance to motion of the controlling digit; and
   wherein the force balancing mechanism includes a clutch controller to control the clutch, and wherein the clutch controller includes a mechanical device that is moved in accordance with the magnitude of the resistance to movement of the controlling digit.

2. A digit mechanism as claimed in claim 1, wherein the controlling digit is the upper digit and the controlled digit is the lower digit.

3. A digit mechanism as claimed in claim 1, wherein the clutch comprises a band brake.

4. A digit mechanism as claimed in claim 1, wherein resistance to movement of a digit increases mechanical forces in the respective rotation mechanism and the clutch controller is moved, directly or indirectly, by the increase in mechanical forces.

5. A digit mechanism as claimed in claim 4, wherein the digit rotation mechanism for the controlling digit is actuated by a cable, such that increased resistance to rotation of the digit will increase the tension in the cable and the clutch controller includes a mechanical device that is moved in accordance with the tension in the cable.

6. A digit mechanism as claimed in claim 1, wherein the force balancing mechanism includes an adjustment/calibration mechanism for adjusting the balance in forces.

7. A digit mechanism as claimed in claim 1, wherein the digit rotation mechanisms for the upper and lower digit comprise a pulley and cable system.

8. A digit mechanism as claimed in claim 7, wherein the pulley and cable system comprises a main cable for receiving a tension force from an actuator in the palm unit and for transferring this to a lower pulley about which the lower digit is arranged to rotate; and a secondary cable also coupled to the lower pulley and arranged to transfer a rotating movement of the lower pulley to an upper pulley about which the upper digit is arranged to rotate.

9. A digit mechanism as claimed in claim 8, wherein the main cable and the secondary cable can be separately disconnected from the lower pulley.

10. A digit mechanism as claimed in claim 8, wherein the force balancing mechanism is arranged to adjust the amount of force transferred between the lower pulley and the lower digit in accordance with resistance to motion of the upper digit around the upper pulley.

11. A digit mechanism as claimed in claim 8, wherein tensions in the main cable and the secondary cable are linked by their connection to the lower pulley, and the upper pulley is coupled to and rotates with the upper digit so that the upper digit has the same degree of rotation as the upper pulley and is actuated by rotation of the upper pulley, with the lower pulley coupled to the lower digit via the force balancing mechanism for partial transfer of the rotation force from the lower pulley to the lower digit.

12. An artificial hand comprising multiple digit mechanisms as claimed in claim 1, the digit mechanisms being mounted to a palm unit that includes actuators for the digit mechanisms.

13. An artificial hand as claimed in claim 12, wherein the actuators are hydraulic actuators.

14. An artificial hand as claimed in claim 13, wherein the hydraulic actuators are coupled together for distribution of pressure between them such that pressure is equalized between the actuators of each of the multiple digit mechanisms.

15. An artificial hand as claimed in claim 12, wherein the digit mechanisms each include an attachment point for a spring that, in use, urges the digit towards the open position, the spring being mounted between the attachment point and a corresponding attachment point on the palm unit of the artificial hand.

16. An artificial hand as claimed in claim 12, wherein the lower digits of each digit mechanism includes a pivot arrangement for mounting to a bracket on a palm unit of the artificial hand.

17. An artificial hand as claimed in claim 12, wherein the palm unit comprises: a palm unit body; a motor held by the palm unit body; a hydraulic pump assembly held by the palm unit body and comprising a low-pressure hydraulic pump and a high-pressure hydraulic pump, wherein both hydraulic pumps are powered simultaneously by the motor; and a hydraulic circuit held by the palm unit body and coupled to both hydraulic pumps, the hydraulic circuit including the actuators for the digit mechanisms.

18. An artificial hand as claimed in claim 17, wherein the hydraulic circuit has a low-pressure configuration in which the discharge sides of both hydraulic pumps are coupled to one or more hydraulic actuator(s) for the artificial hand and a high-pressure configuration in which the discharge side of the low-pressure pump is isolated from the hydraulic actuator(s) and recirculates fluid to the suction side of the low pressure pump with the discharge side of the high-pressure pump remaining coupled to the hydraulic actuator(s).

19. A method for control of a digit mechanism of an artificial hand the digit mechanism comprising:
   a lower digit arranged to be rotatably coupled to a palm unit of the artificial hand;
   an upper digit rotatably coupled to the lower digit;
   a lower digit rotation mechanism for applying a moment to the lower digit to rotate the lower digit relative to the palm unit;
   an upper digit rotation mechanism for applying a moment to the upper digit to rotate the upper digit relative to the lower digit; and
   a force balancing mechanism arranged so that if there is no resistance to closing motion of the upper digit or the lower digit then both digits will rotate about their respective rotation mechanisms at the same time, the force balancing mechanism providing mechanical adjustment of the magnitude of the moment applied by the lower digit rotation mechanism and/or the upper digit rotation mechanism in accordance with the magnitude(s) of outside forces resisting rotation of the upper digit and/or the lower digit in order to preferentially apply movement to the digit experiencing lower resistance to movement so that either digit is able to rotate whilst rotation of the other digit is stopped;
   wherein the force balancing mechanism is arranged to increase the force applied to rotate a controlled digit which is one of the upper digit or the lower digit when a controlling digit, which is the other of the upper digit or the lower digit experiences a greater resistance to movement than the controlled digit, and decrease the force applied to rotate the controlled digit when the controlling digit experiences a lesser resistance to movement than the controlled digit;
   wherein the lower digit rotation mechanism and upper digit rotation mechanism are arranged to be mechanically actuated, in use, by a force applied from a single actuator at the palm unit;
   wherein the force balancing mechanism includes a clutch for transmission of a varying amount of power for rotation of the controlled digit with the clutch being controlled to adjust the varying amount of power in accordance with the degree of resistance to motion of the controlling digit; and
   wherein the force balancing mechanism includes a clutch controller to control the clutch, and wherein the clutch controller includes a mechanical device that is moved in accordance with the magnitude of the resistance to movement of the controlling digit wherein the digit mechanism includes the method comprising:
   mechanically actuating the lower digit rotation mechanism and upper digit rotation mechanism using a force applied from a single actuator at the palm unit; and
   mechanically adjusting the magnitude of the moment applied by the lower digit rotation mechanism and/or the upper digit rotation mechanism in accordance with the magnitude(s) of outside forces resisting rotation of the upper digit and/or the lower digit in order to preferentially apply movement to the digit experiencing lower resistance to movement, thereby increasing the force applied to rotate a controlled digit when a controlling digit experiences a greater resistance to movement than the controlled digit, and decreasing the force applied to rotate the controlled digit when the controlling digit experiences a lesser resistance to movement than the controlled digit.

20. A method as claimed in claim 19, wherein the controlling digit is the upper digit and the controlled digit is the lower digit.

21. A method as claimed in claim 19, including using a clutch for transmission of a varying amount of power for rotation of the controlled digit, and controlling the clutch to adjust the varying amount of power in accordance with the degree of resistance to motion of the controlling digit.

* * * * *